US008673359B2

(12) United States Patent
Cho et al.

(10) Patent No.: US 8,673,359 B2
(45) Date of Patent: Mar. 18, 2014

(54) NANOPARTICLE COMPOSITIONS AND METHODS FOR IMPROVED ORAL DELIVERY OF ACTIVE AGENTS

(75) Inventors: Daniel Cho, Providence, RI (US); Joshua Reineke, Providence, RI (US); Edith Mathiowitz, Brookline, MA (US); Bryan Laulicht, Cambridge, MA (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 13/179,205

(22) Filed: Jul. 8, 2011

(65) Prior Publication Data

US 2012/0009267 A1    Jan. 12, 2012

Related U.S. Application Data

(60) Provisional application No. 61/362,615, filed on Jul. 8, 2010.

(51) Int. Cl.
*A61K 9/50* (2006.01)
*A61K 38/02* (2006.01)
*A61K 48/00* (2006.01)
*A61K 47/34* (2006.01)

(52) U.S. Cl.
USPC ........... 424/497; 514/9.7; 514/1.1; 514/772.3

(58) Field of Classification Search
USPC ............... 424/497; 514/9.7, 1.1, 772.3, 772.4
See application file for complete search history.

(56) References Cited

U.S. PATENT DOCUMENTS

| | | | |
|---|---|---|---|
| 3,266,987 A | 8/1966 | Crowley | |
| 3,960,757 A | 6/1976 | Morishita | |
| 4,460,563 A | 7/1984 | Calanchi | |
| 4,757,128 A | 7/1988 | Domb | |
| 4,794,000 A | 12/1988 | Ecanow | |
| 4,997,904 A | 3/1991 | Domb | |
| 5,019,400 A | 5/1991 | Gombotz | |
| 5,175,235 A | 12/1992 | Domb | |
| 5,912,017 A | 6/1999 | Mathiowitz | |
| 6,143,211 A | 11/2000 | Mathiowitz | |

(Continued)

FOREIGN PATENT DOCUMENTS

| | | |
|---|---|---|
| WO | 9321906 | 11/1993 |
| WO | 2009075652 | 6/2009 |

OTHER PUBLICATIONS

Beck, et al., "New long-acting injectable microcapsule contraceptive system", Am J Obstet Gynecol,135(3):419-26 (1979).

(Continued)

*Primary Examiner* — Aradhana Sasan
(74) *Attorney, Agent, or Firm* — Pabst Patent Group LLP

(57) ABSTRACT

Nanoparticles, compositions, and methods for the improved uptake of active agents are disclosed herein. The compositions contain a monodisperse population of nanoparticles, preferably including an active agent, where the nanoparticles are formed from a polymeric material possessing specified bioadhesion characteristics. Following enteral administration, preferably oral administration, the nanoparticles exhibit total intestinal uptakes of greater than 20%, preferably greater than 45%, more preferably greater than 65%. When compared to uptake of the same compositon in the absence of the bioadhesive polymeric material, the nanoparticles have significantly increased uptake with intestinal uptake of the increased by more than 100%, preferably even greater than 500%. Further disclosed herein is a method of producing multi-walled nanoparticles, as well as methods of using thereof. Multi-walled particles prepared using the method disclosed herein are useful for controlling the release of active agents.

18 Claims, 6 Drawing Sheets

(56) References Cited

U.S. PATENT DOCUMENTS

| | | |
|---|---|---|
| 6,235,313 B1 | 5/2001 | Mathiowitz |
| 6,368,586 B1 * | 4/2002 | Jacob et al. ............... 424/78.08 |
| 6,620,617 B2 | 9/2003 | Mathiowitz |
| 2005/0064027 A1 * | 3/2005 | Jacob et al. ................ 424/451 |
| 2005/0201974 A1 | 9/2005 | Schestopol |

OTHER PUBLICATIONS

Beck, et al., "A new long-acting injectable microcapsule system for the administration of progesterone", Fertil. Steril., 31:545-51 (1979).

Benita, et al., "Characterization of drug-loaded poly(d,l-lactide) microspheres", J. Pharm. Sci., 73:1721-4 (1984).

Mathiowitz, et al., "Novel microcapsules for delivery",Systems, Reactive Polymers, 6:275-83 (1987).

Mathiowitz, et al, "Morphology of polyanhydride microsphere delivery systems", J. Scanning Microsc, 4:329-40 (1990).

Ponchel, et al., "Specific and non-specific bioadhesive particulate systems for oral delivery to the gastrointestinal tract", Adv Drug Deliv Rev., 34:191-219 (1998).

Sawhney, et al., "Bioerodible hydrogels based on photopolymerized poly (ethylene glycol)-co-poly(.alpha.-hydroxy acid) diacrylate macromers" , Macromolecules, 26:581-87 (1993).

* cited by examiner

Polycarbophil

NANOPARTICLE COMPOSITIONS AND METHODS FOR IMPROVED ORAL DELIVERY OF ACTIVE AGENTS

CROSS REFERENCE TO RELATED APPLICATIONS

This application claims benefit of U.S. Provisional Application No. 61/362,615, filed Jul. 8, 2010, which is hereby incorporated herein by reference in its entirety.

FIELD OF THE INVENTION

This invention is in the field of nanoparticles for improved drug delivery.

BACKGROUND OF THE INVENTION

The use of microparticles and nanoparticles for drug delivery is well known in the art. Specifically, microsphere and nanosphere-based polymeric drug delivery systems have great potential as oral delivery systems due to their ability to protect encapsulated active agents from the harsh gastrointestinal tract. Although significant effort has focused on developing effective delivery systems for translation into clinical use, significant obstacles exist in the development of effective nanoparticles for oral drug delivery.

One significant obstacle facing microsphere and nanosphere-based oral delivery systems is achieving high enough levels of uptake to reach therapeutic concentrations of the encapsulated drugs after administration. A variety of strategies have been evaluated to enhance the translocation of particles from the intestinal lumen, most with limited success. One potential method of enhancing uptake is to employ polymers with bioadhesive properties. In theory, incorporating such polymers will result in particles which adhere to the mucous membrane proximal to the intestinal cells, and increase the transit time of the particles in the gastrointestinal tract. While many hydrogel-based bioadhesive platforms have shown promise for oral drug delivery systems (Ponchel, et al. *Adv Drug Deliv Rev.* 34:191-219 (1998)), their success has been limited due to the rapid release of drugs upon aqueous swelling as well as difficulties associated with loading hydrophilic drugs into the hydrogels. In addition, bioadhesive polymer chains often become physically entangled in the mucus, impeding the translocation of the particles in the gastrointestinal tract. Peppas, et al., *Biomaterials,* 17:1553-61 (1996).

Another obstacle facing microsphere and nanosphere-based oral delivery systems is providing accurate control of drug release kinetics. Microparticles and nanoparticles often exhibit burst release, i.e., release of a large amount of the encapsulated drug shortly after administration of the particles. Burst release occurs because some of the drug to be encapsulated adheres to the surface of the particle during preparation and/or some of the drug diffuses to the surface prior to administration. Upon administration, the drug on the surface is released almost immediately since there is no layer or coating to control release of the drug.

In order to overcome burst release phenomena, microparticles and nanoparticles have been coated with controlled release coatings using conventional coating techniques. While such techniques have been used to successfully coat microparticles, it has been a challenge to modify these techniques to effectively coat nanoparticles due to their smaller size.

Alternatives to coating nanoparticles using conventional coating techniques include methods for preparing multiwall nanoparticles in situ. However, many of these techniques require multiple relatively complicated steps. For example, U.S. Pat. No. 5,912,017 to Mathiowitz, et al., describes methods for making multi-walled microspheres. Two polymers are dissolved in a volatile organic solvent. The substance to be encapsulated is dispersed or dissolved in the polymer solution and the mixture of polymers and substance to be encapsulated in suspended in an aqueous solution. The organic solvent is removed by slow evaporation or spray drying to form the microsphere. Alternatively, the microspheres can be formed from a melt.

WO 2009/075652 to Nanyang Technological University, et al., describes a procedure for the formation of multi-walled microspheres involving emulsifying a first polymer solution in an organic solvent having at least one hydrophilic agent emulsified therein and a second solvent solution in an organic solvent; emulsifying the emulsion of the polymers and agent with an aqueous solution containing a stabilizer; and removing the organic solvents. This procedure requires multiple steps to form multiple emulsions.

Therefore, it is an object of the invention to provide compositions which exhibit increased uptake in the gastrointestinal tract.

It is a further object of the invention to provide methods for increasing the uptake in the gastrointestinal tract of active agents.

It is a further object of the invention to provide improved multi-walled nanoparticles, as well as improved methods for making multi-walled nanoparticles, particularly methods that form the nanoparticles in a minimum number of steps and do not require emulsification of the solvent.

It is yet a further object of the invention to provide improved multi-walled nanoparticles containing a bioadhesive layer.

SUMMARY OF THE INVENTION

Disclosed herein are nanoparticle compositions that exhibit increased intestinal uptake in vivo. The nanoparticle compositions include a monodisperse plurality of nanoparticles formed from a polymeric material. In preferred embodiments, the nanoparticles also contain one or more active agents dispersed or encapsulated therein.

In some embodiments, the nanoparticles are formed from a bioadhesive polymeric material. The preferred bioadhesive polymers (1) possess a higher adhesion to freshly excised rat intestinal tissue, as measured in terms of fracture strength using the assay described in Example 3, than polymethyl methacrylate (PMMA), more preferably equivalent to or higher than polysytyrene (PS); (2) exhibit a lower contact angle with rat mucin than PMMA, more preferably equivalent to or lower than PS; and (3) when formed into nanoparticles, exhibit a higher binding ratio to the jejunum, as measured by the everted sac method described in Example 3, than PMMA nanoparticles of substantially equivalent mean particle size, more preferably equivalent to or higher than PS nanoparticles of substantially equivalent mean particle size.

In preferred embodiments, the nanoparticles in the composition exhibit a total intestinal uptake of greater than 45%, more preferably greater than 60%, most preferably greater than 65%.

Also disclosed is a method increasing uptake of nanoparticles in the gastrointestinal tract of a patient in need of treatment. The method includes orally administering to a patient in need thereof a composition comprising a plurality of nanoparticles, preferably the nanoparticles contain one or more active agents. The compositions also contain a pharmaceutically acceptable carrier. Optionally, the nanoparticles are included in a matrix or hydrogel. The nanoparticles are preferably bioadhesive nanoparticles, having the three above-described properties.

In preferred embodiments, the total intestinal uptake of the polymeric nanoparticles is greatly increased compared to the same composition in the absence of the bioadhesive polymeric material. In preferred embodiments, method increases total intestinal uptake of the nanoparticles in the composition by more than 500%, as compared to the total intestinal uptake of the same nanoparticles without a bioadhesive polymeric material having the three above-described properties.

Further disclosed herein are methods for the formation of multi-walled nanoparticles, such as double-walled nanospheres. The double-walled nanoparticles are generally formed in a single step. Multi-walled particles can be produced by performing multiple sequential phase inversions. For double-walled particles, a first polymer, generally referred to herein as the "core polymer", is dissolved in a first solvent to form a core polymer solution. The first solvent is selected such that it is a solvent for the core polymer and a second polymer, generally referred to herein as the "shell polymer".

If one or more active agents are to be encapsulated in the multi-walled particles, the active agents are dissolved or dispersed in the core polymer solution. The agent can be introduced into the core polymer solution as a liquid or a solid. Alternatively, the agent to be encapsulated can be emulsified and the emulsion introduced to the core polymer solution. The shell polymer is dissolved in a second solvent, which is not a solvent for the core polymer, to form a shell polymer solution. The core polymer solution and the shell polymer solution are combined and added to a third solvent, which is a non-solvent for the core polymer and the shell polymer, to form the nanoparticles. The resulting nanoparticles can be cured prior to filtering the particles from the solvent.

The core polymer and the shell polymer can independently be a biodegradable polymer or a non-biodegradable polymer. In one embodiment, the core polymer is a biodegradable polymer and the shell polymer is a biodegradable polymer. In another embodiment, the core polymer is a non-biodegradable polymer and the shell polymer is a non-biodegradable polymer.

In another embodiment, the core polymer is a non-biodegradable polymer and the shell polymer is a biodegradable polymer. In still another embodiment, the shell polymer is a bioadhesive polymer.

The multi-walled nanoparticles prepared using the method described herein can be used for controlled drug delivery. For example, a therapeutic, diagnostic, and/or prophylactic agent can be encapsulated in a multi-walled nanoparticle having a biodegradable core polymer and a biodegradable shell polymer. In a preferred embodiment, the shell polymer is bioadhesive. The nanoparticles can also be used in applications wherein the agent remains encapsulated within the multi-walled particle, i.e., the core and/or shell polymers are not degradable. Such applications include, but are not limited to, bioimaging.

The methods described herein produce multi-walled nanoparticles which minimize the burst effect commonly seen with micro- and nanospheres as well as modify surface chemistry for the enhancement of particle uptake from the gastrointestinal system.

DETAILED DESCRIPTION OF THE INVENTION

Figure 1A:
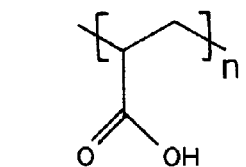
FIG. 1 shows the chemical structures of polymers tested for bioadhesive properties: (a) Chemical structure of a generalized acrylic acid polymer such as Polycarbophil; (b) reaction scheme for reacting maleic anhydride monomer with a hydroxyl aromatic compound containing an amino group; (c) Chemical structures of Polycarbophil AA-1 (Polycarbophil) and bioadhesive poly(butadiene-co-maleic anhydride) (PBMA) poly(butadiene maleic anhydride-co-phenylalanine) (PBMAP), poly(butadiene maleic anhydride-co-tyrosine) (PBMAT), and poly(butadiene maleic anhydride-co-L-dopamine) (PBMAD); (d) Chemical structures of poly (ethylene maleic anhydride) (PEMA), poly(ethylene maleic anhydride-co-phenylalanine) (PEMAP), poly(ethylene maleic anhydride-co-tyrosine) (PEMAT), and poly(ethylene maleic anhydride-co-L-dopamine) (PEMAD).
Figure 1B:
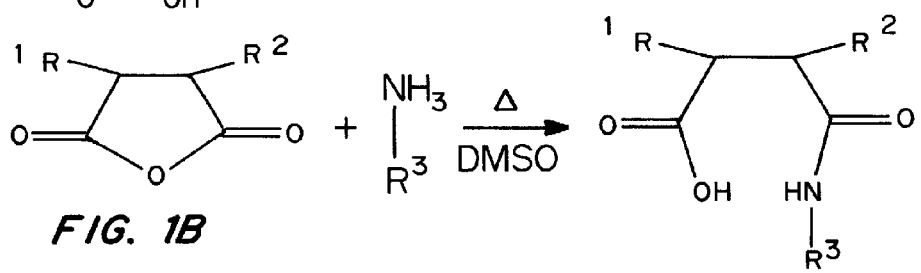
Figure 1C:
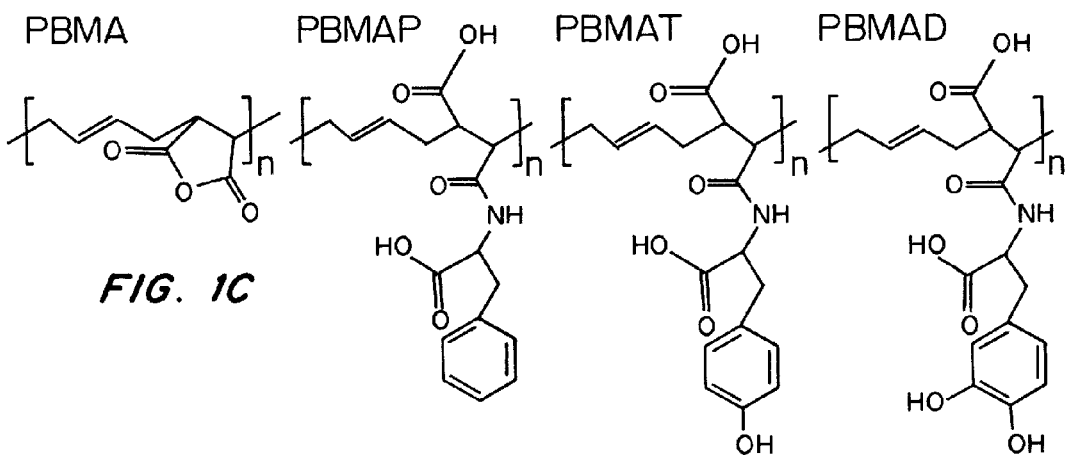
Figure 1D:
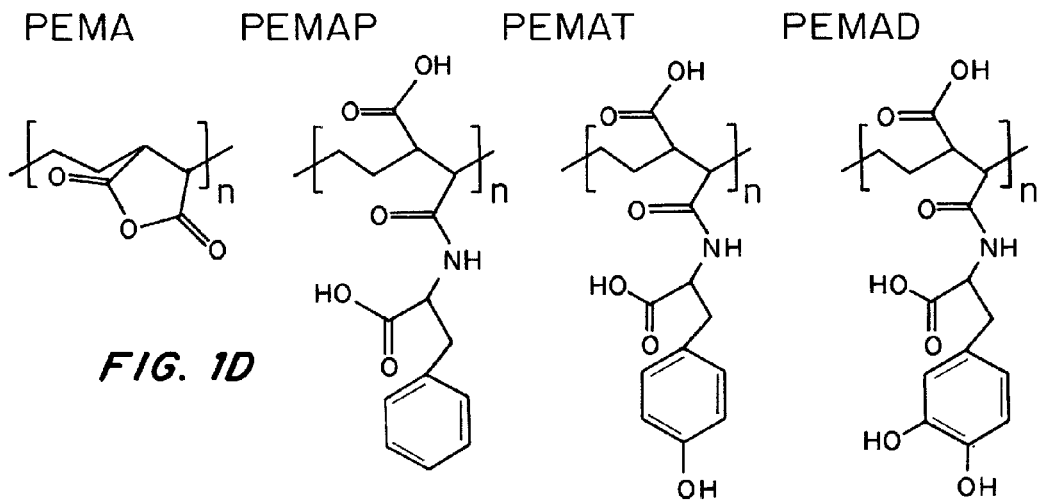

Described herein are nanoparticle compositions, useful for oral drug delivery applications, which exhibit increased total intestinal uptake. Also described herein are methods for improving total intestinal uptake of nanoparticles, preferably containing one or more active agents. The nanoparticles are formed from a polymeric material possessing specified bioadhesion characteristics.

Further disclosed herein is a method of producing multi-walled nanoparticles, as well as methods of using thereof. Multi-walled particles prepared using the method disclosed herein are useful for controlling the release of active agents.

I. Definitions

"Nanoparticle", as used herein, generally refers to a particle having a diameter from about 10 nm to about 1 micron, preferably from 100 nm to about 1 micron. In one embodiment, the particles have a size range from about 500 to about 600 nm. The particles can have any shape but are generally spherical in shape. Nanoparticles having a spherical shape are generally referred to as "nanospheres".

"Core polymer", as used herein, generally refers to the polymer which forms the innermost wall in a multi-walled nanoparticle.

"Shell polymer", as used herein, generally refers to the polymer which forms the outermost wall in a multi-walled nanoparticle.

"Core polymer solvent", as used herein, generally refers to a solvent in which both the core polymer and polymer used to form the next wall in a multi-walled nanoparticle, e.g. the shell polymer in a double-walled nanoparticle, are generally soluble at the operating conditions. In one embodiment, the operating conditions are standard temperature (25° C.) and pressure (1 atm); however, these conditions may vary depending on the nature of the polymer-solvent pairs.

"Shell polymer solvent", as used herein, generally refers to a solvent in which the shell polymer is soluble at the operating conditions. and the core polymer and any other polymers used to form the multi-walled nanoparticles are insoluble at the operating conditions. In one embodiment, the operating conditions are standard temperature (25° C.) and pressure (1 atm); however, these conditions may vary. For example, changes in temperature can be used to initiate phase separation of one or more polymers.

"Non-solvent", as used herein, generally refers to a solvent in which all of the polymers used to form the multi-walled nanoparticle are insoluble at the operating conditions. For example, with respect to double walled nanoparticles, both the core polymer and the shell polymer are generally insoluble in the non-solvent. In one embodiment, the operating conditions are standard temperature (25° C.) and pressure (1 atm); however, these conditions may vary. For example, differences in solubility at different temperatures can be used to initiate the phase change for a given polymer.

"Cloud point", as used herein, generally refers to the concentration of a solvent in a mixture of two or more solvents containing two or more polymers dissolved therein, at which one of the polymers is no longer completely soluble and precipitates from the solvent mixture as a distinct phase. The cloud point is generally observed as a transition from a translucent to a metastable cloudy turbid state due to the separation of the solution into two distinct phases, one with a high relative polymer concentration and another with a low relative polymer concentration. For example, with respect to a mixture of a core polymer solvent and a shell polymer solvent in which the core polymer and shell polymer are dissolved, the cloud point refers to the concentration of the shell polymer solvent at which the core polymer is no longer completely soluble and precipitates from the mixture as a distinct phase. The cloud point can also be reached by varying the temperature and/or addition of an excipient that induces phase separation, such as a salt.

"Bioactive agent" and "active agent" are used interchangeably herein and include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment. Examples include, but are not limited to, small-molecule drugs, peptides, proteins, antibodies, sugars, polysaccharides, nucleotides, oligonucleotides, aptamers, siRNA, nucleic acids, and combinations thereof "Bioactive agent" includes a single such agent and is also intended to include a plurality of bioactive agents including, for example, combinations of two or more bioactive agents "Copolymer" as used herein, generally refers to a single polymeric material that is comprised of two or more different monomers. The copolymer can be of any form, such as random, block, graft, etc. The copolymers can have any end-group, including capped or acid end groups.

"Sufficient" and "effective" are used interchangeably herein and, generally refer to an amount (e.g. mass, volume, dosage, concentration, and/or time period) needed to achieve one or more desired result(s).

"Biocompatible" as used herein, generally refers to a material and any metabolites or degradation products thereof that are generally non-toxic to the recipient and do not cause any significant adverse effects to the subject.

"Biodegradable" as used herein, generally refers to a material that will degrade or erode under physiologic conditions to smaller units or chemical species that are capable of being metabolized, eliminated, or excreted by the subject. The degradation time is a function of polymer composition and morphology. Suitable degradation times are from days to weeks. For example, the polymer may degrade over a time period from seven days to 24 weeks, preferably seven days to twelve weeks, preferably from seven days to six weeks, preferably from seven days to three weeks.

"Molecular weight" as used herein, generally refers to the relative average chain length of the bulk polymer, unless otherwise specified. In practice, molecular weight can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size" as used herein, generally refers to the statistical mean particle size (diameter) of the particles in the composition. Two populations can be said to have a "substantially equivalent mean particle size" when the statistical mean particle size of the first population of nanoparticles is within 20% of the statistical mean particle size of the second population of nanoparticles; more preferably within 15%, most preferably within 10%.

"Controlled release" and "modified release", are used interchangeably herein and generally refer to a release profile in which the active agent release characteristics of time course and/or location are chosen to accomplish therapeutic or convenience objectives not offered by conventional dosage forms such as solutions, suspensions, or promptly dissolving dosage forms. Delayed release, extended release, and pulsatile release and their combinations are examples of modified release.

"Excipient" as used herein, generally includes any other compound that can be contained in, on, or in combination with the nanoparticle that is not a therapeutically or biologically active compound. As such, an excipient should be pharmaceutically or biologically acceptable or relevant, for example, an excipient should generally be non-toxic to the subject. "Excipient" includes a single such compound and is also intended to include a plurality of compounds.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% of the distribution lies within 5% of the median particle size.

"Pharmaceutically Acceptable Carrier", as used herein, refers to all components of a pharmaceutical composition which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

"Total Intestinal Uptake", as used herein, refers to the percentage of nanoparticles in an administered dosage which translocate from the intestinal lumen of a patient into other tissues of the body. Total intestinal uptake, as used herein, is quantified using the in vivo isolated loop assay described in Example 4. The total intestinal uptake (as a percent) is calculated by dividing the sum of the amount of nanoparticles detected in the tissues of the body (excluding isolated loop and loop rinse samples) by the total dose administered into the isolated intestinal loop of the model, and multiplying by 100.

"Percent increase in Total Intestinal Uptake", as used herein, refers to comparing the total intestinal uptake of a composition containing a bioadhesive polymeric material with the total intestinal uptake of the nanoparticles in the same composition, in the absence of the above-described polymeric material. For example, as described in Example 4, PMMA-BMAD nanospheres exhibited a total intestinal uptake of 66.9±12.9% of the administered dose, whereas PMMA nanospheres exhibited a total intestinal uptake of 5.8±1.9% of the administered dose. The percent increase in total intestinal uptake is calculated by dividing the net increase in intestinal uptake (i.e. the percent intestinal uptake of the PMMA-BMAD nanospheres minus the percent intestinal uptake of the PMMA nanospheres) by the intestinal uptake of the nanoparticles in the same composition, in the absence of the above-described polymeric material (i.e. the percent intestinal uptake of the PMMA nanospheres), and multiplying by 100. Accordingly, the increase in total intestinal uptake upon inclusion of BMAD in the composition is calculated to be at least 600%.

"Patient", as used herein, refers to either a human or non-human animal treated using the nanoparticles, compositions, and methods described herein. In preferred embodiments, the patient is a human.

II. Nanoparticle Compositions for Increased Intestinal Uptake

Described herein are nanoparticle compositions which exhibit increased intestinal uptake in vivo. The compositions include a monodisperse plurality of nanoparticles formed from a polymeric material. The polymeric material can be a polymer, a copolymer, or a polymer blend (i.e. a physical mixture of one or more polymers and/or copolymers). The polymeric material has the following characteristics: (1) possesses a higher adhesion to freshly excised rat intestinal tissue, as measured in terms of fracture strength using the assay described in Example 3, than PMMA; (2) exhibits a lower contact angle with rat mucin than PMMA; and (3) when formed into spherical nanoparticles, exhibits a higher binding ratio to the jejunum, as measured by the everted sac method as described in Example 3, than PMMA nanoparticles of substantially equivalent mean particle size.

In preferred embodiments, the composition includes a monodisperse plurality of nanoparticles formed from a polymeric material, wherein the polymeric material (1) possesses an adhesion to freshly excised rat intestinal tissue, as measured in terms of fracture strength using the assay described in Example 3, that is equivalent to or greater than PS; (2) exhibits a contact angle with rat mucin that is equivalent to or less than the contact angle for PS; and (3) when formed into spherical nanoparticles, exhibits a binding ratio to the jejunum, as measured by the everted sac method as described in Example 3, that is equivalent to or greater than PS nanoparticles of substantially equivalent mean particle size.

Exemplary polymeric materials that have the characteristics listed above include, but are not limited to, bioadhesive polymers such as those described in U.S. Pat. No. 6,235,313 to Mathiowitz et al. Suitable polymers include non-water-soluble polyacrylates and polymethacrylates; polymers of hydroxy acids, such as polylactide [such as polylactic acid (2 kDa MW, types SE and HM)] and polyglycolide; polyanhydrides; polyorthoesters; polysytyrene (PS), poly(ethylene-co-maleic anhydride), poly(ethylene maleic anhydride-co-L-dopamine), poly(ethylene maleic anhydride-co-phenylalanine), poly(ethylene maleic anhydride-co-tyrosine), poly(butadiene-co-maleic anhydride), poly(butadiene maleic anhydride-co-L-dopamine) (pBMAD), poly(butadiene maleic anhydride-co-phenylalanine), poly(butadiene maleic anhydride-co-tyrosine), poly(fumaric-co-sebacic)anhydride (P(FA:SA)), poly(bis carboxy phenoxy propane-co-sebacic anhydride) (20:80) (poly(CCP:SA)), alginate (freshly prepared); and poly(fumaric anhydride-co-sebacic anhydride (20:80) (p[FA:SA]), copolymers of p[FA:SA] (50:50) and non-water-soluble polyacrylates and polyacrylamides, as well as blends comprising these polymers; and copolymers comprising the monomers of these polymers.

In designing bioadhesive polymeric nanoparticles based on polylactides, polymers that have high concentrations of carboxylic acid are preferred. This can be accomplished by using low molecular weight polymers (Mw 2000), since low molecular weight polymers contain high concentration of carboxylic acids at the end groups.

Blending or copolymerization sufficient to provide a certain amount of hydrophilic character can be useful to improve wettability of the materials. For example, about 5% to about 20% of monomers may be hydrophilic monomers. Preferably, the polymers are bioerodable, with preferred molecular weights ranging from 1000 to 50,000 Da, and most preferably 2000 to 20,000 Da.

In some embodiments, the nanoparticle composition exhibits a total intestinal uptake, as measured using the in vivo isolated loop assay described in Example 4, of greater than 6%, 10%, 15%, 20%, 25%, 30%, 35%, 40%, 45%, 50%, 55%, 60%, 65%, 70%, or 75%. In preferred embodiments, the composition exhibits a total intestinal uptake of greater that 25%, preferably greater than 45%, more preferably greater than 50%, more preferably greater than 60%, most preferably greater than 65%.

In some embodiments, the polymeric material exhibits adhesion to freshly excised rat intestinal tissue, as measured in terms of fracture strength using the assay described in Example 3, of greater than 100, 110, 120, 130, 140, 150, 160, 170, 180, 190, 200, 210, 220, 230, 240, or 250 mN/cm$^2$. In particularly preferred embodiments, the polymeric material exhibits adhesion to freshly excised rat intestinal tissue, as measured in terms of fracture strength using the assay described in Example 3, of greater than 110 mN/cm$^2$, more preferably greater than 150 mN/cm$^2$, most preferably greater than 200 mN/cm$^2$.

In some embodiments, the polymeric material exhibits a contact angle with rat mucin of less than 50, 45, 40, 39, 38, 37, 36, 35, 34, 33, 32, 31, 30, 29, 28, 27, 26, 25, 24, 23, 22, 21, or 20°. In preferred embodiments, the polymeric material exhibits a contact angle with rat mucin of less than 40°, more preferably less than 37°, more preferably less than 35°, more preferably less than 32°, and most preferably less than 30°.

In some embodiments, the polymeric material, when formed into spherical nanoparticles, exhibits a binding ratio to the jejunum, as measured by the everted sac method as described in Example 3, of greater than 1.5, 1.75, 2.0, 2.25, 2.5, 2.75, 3.0, 3.25, 3.5, 3.75, or 4.0. In preferred embodiments, the polymeric material, when formed into spherical nanoparticles, exhibits a binding ratio to the jejunum, as measured by the everted sac method as described in Example 3, of greater than 1.75, more preferably greater than 2.0, more preferably greater than 2.5, most preferably greater than 3.0.

A. Pharmaceutically Acceptable Carriers

The compositions disclosed herein include a monodisperse plurality of nanoparticles dispersed or suspended in a pharmaceutically acceptable carrier. Pharmaceutically acceptable carriers include, but are not limited to, diluents, preservatives, binders, lubricants, disintegrators, swelling agents, fillers, stabilizers, and combinations thereof. Pharmaceutically acceptable carriers also include all components of any coating formed around the nanoparticle composition, which may include plasticizers, pigments, colorants, stabilizing agents, and glidants. Pharmaceutically acceptable carriers are known in the art, and described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995).

1. Bioadhesive Matrix

In preferred embodiments, the composition includes a bioadhesive matrix in which the nanoparticles are dispersed. In these embodiments, the bioadhesive matrix promotes contact between the mucosa of the gastrointestinal tract and the nanoparticles. Other suitable bioadhesive polymers are described in U.S. Pat. No. 6,235,313 to Mathiowitz et al., the teachings of which are incorporated herein by reference, and include polyhydroxy acids, such as poly(lactic acid), polystyrene, polyhyaluronic acids, casein, gelatin, glutin, polyanhydrides, polyacrylic acid, alginate, chitosan; polyacrylates, such as poly(methyl methacrylates), poly(ethyl methacrylates), poly butylmethacrylate), poly(isobutylmethacrylate), poly(hexlmethacrylate), poly(isodecl methacrylate), poly(lauryl methacrylate), poly(phenyl methacrylate), poly(methyl acrylate), poly(isopropyl acrylate), poly(isobutyl acrylate), and poly (octadecl acrylate); polyacrylamides; poly(fumaric-co-sebacic)acid, poly(bis carboxy phenoxy propane-co-sebacic anhydride), polyorthoesters, and copolymers, blends and mixtures thereof.

In particularly preferred embodiments, the matrix is a bioerodible, bioadhesive matrix. Suitable bioerodible, bioadhesive polymers include bioerodible hydrogels, such as those described by Sawhney, et al., in *Macromolecules,* 1993, 26:581-587, the teachings of which are incorporated herein by reference. Representative bioerodible, bioadhesive polymers include, but are not limited to, synthetic polymers such as poly hydroxy acids, such as polymers of lactic acid and glycolic acid, polyanhydrides, poly(ortho)esters, polyesters, polyurethanes, poly(butic acid), poly(valeric acid), poly(caprolactone), poly(hydroxybutyrate), poly(lactide-co-glycolide), poly(lactide-co-caprolactone), poly(ethylene-co-maleic anhydride), poly(ethylene maleic anhydride-co-L-dopamine), poly(ethylene maleic anhydride-co-phenylalanine), poly(ethylene maleic anhydride-co-tyrosine), poly(butadiene-co-maleic anhydride), poly (butadiene maleic anhydride-co-L-dopamine) (pBMAD), poly(butadiene maleic anhydride-co-phenylalanine), poly(butadiene maleic anhydride-co-tyrosine), poly(fumaric-co-sebacic)anhydride (P(FA:SA)), poly(bis carboxy phenoxy propane-co-sebacic anhydride) (20:80) (poly(CCP:SA)), as well as blends comprising these polymers; and copolymers comprising the monomers of these polymers, and natural polymers such as alginate and other polysaccharides, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers, blends and mixtures thereof. In general, these materials degrade either by enzymatic hydrolysis or exposure to water in vivo, by surface or bulk erosion.

In particularly preferred embodiments, the nanoparticles are suspended in a matrix which is a copolymer of maleic anhydride and butadiene containing DOPA, tyrosine, and/or phenyl alanine groups. In another embodiment, the matrix is a copolymer of maleic anhydride and ethylene containing DOPA, tyrosine, and/or phenyl alanine groups. Other suitable monomers that can be copolymerized with maleic anhydride include vinyl acetate and styrene.

B. Agents

In some embodiments, the compositions described herein further contain one or more agents encapsulated or dispersed within the nanoparticles and/or dissolved or dispersed in the pharmaceutically acceptable carrier.

Suitable agents include, but are not limited to, adhesives, gases, pesticides, herbicides, fragrances, antifoulants, dies, salts, oils, inks, cosmetics, catalysts, detergents, curing agents, flavors, foods, fuels, metals, paints, photographic agents, biocides, pigments, plasticizers, propellants, dyes, colorants, as well as biologically active agents (i.e. active agents), such as therapeutic agents, prophylactic agents, and diagnostic agents, and combinations thereof.

For orally administered formulations, the agent is a therapeutic agent, prophylactic agent, or diagnostic agent, or combination thereof.

The loading range for the agent within the nanoparticles is from about 0.01 to about 80% (agent weight/polymer weight), preferably from 0.01% to about 50% (wt/wt), more preferably from about 0.01% to about 25% (wt/wt), even more preferably from about 0.01% to about 10% (wt/wt), most preferably from about 0.1% to about 5% (wt/wt). For small molecules, the percent loading is typically from about 0.01% to about 20% (wt/wt), although higher loadings may be achieved for cores containing agent alone without polymer and/or for hydrophobic drugs and/or insoluble metals.

For large biomolecules, such as proteins and nucleic acids, typical loadings are from about 0.01% to about 5% (wt/wt), preferably from about 0.01% to about 2.5% (wt/wt), more preferably from about 0.01% to about 1% (wt/wt).

1. Therapeutic, Diagnostic, and/or Prophylactic Agents

In one embodiment, the agent to be encapsulated is a biologically active agent. Suitable biologically active agents include, but are not limited to: adrenergic agents; adrenocortical steroids; adrenocortical suppressants; aldosterone antagonists; amino acids; anabolics; analeptics; analgesics; anesthetics; anorectics; anti-acne agents; anti-adrenergics; anti-allergics; anti-amebics; anti-anemics; anti-anginals; anti-arthritics; anti-asthmatics; anti-atherosclerotics; antibacterials; anticholinergics; anticoagulants; anticonvulsants; antidepressants; antidiabetics; antidiarrheals; antidiuretics; anti-emetics; anti-epileptics; antifibrinolytics; antifungals; antihemorrhagics; antihistamines; antihyperlipidemias; antihypertensives; antihypotensives; anti-infectives; anti-inflammatory agents; antimicrobials; antimigraines; antimitotics; antimycotics; antinauseants; antineoplastics; antineutropenics, antiparasitics; antiproliferatives; antipsychotics; antirheumatics; antiseborrheics; antisecretory agents; antispasmodics; antithrombotics; anti-ulceratives; antivirals; appetite suppressants; blood glucose regulators; bone resorption inhibitors; bronchodilators; cardiovascular agents; cholinergic agents; depressants; diagnostic aids; diuretics; dopaminergic agents; estrogen receptor agonists; fibrinolytics; fluorescent agents; free oxygen radical scavengers; gastrointestinal motility effectors; glucocorticoids; hair growth stimulants; hemostatics; histamine H2 receptor antagonists; hormones; hypocholesterolemics; hypoglycemics; hypolipidemics; hypotensives; imaging agents; immunizing agents; immunomodulators; immunoregulators; immuno stimulants; immunosuppressants; keratolytics; leutinizing hormone releasing hormone (LHRH) agonists; mood regulators; mucolytics; mydriatics; nasal decongestants; neuromuscular blocking agents; neuroprotectives; NMDA antagonists; non-hormonal sterol derivatives; plasminogen activators; platelet activating factor antagonists; platelet aggregation inhibitors; psychotropics; radioactive agents; scabicides; sclerosing agents; sedatives; sedative-hypnotics; selective adenosine A1 antagonists; serotonin antagonists; serotonin inhibitors; serotonin receptor antagonists; steroids; thyroid hormones; thyroid inhibitors; thyromimetics; tranquilizers; amyotrophic lateral sclerosis agents; cerebral ischemia agents; Paget's disease agents; unstable angina agents; vasoconstrictors; vasodilators; wound healing agents; and xanthine oxidase inhibitors.

Bioactive agents include immunological agents such as allergens (e.g., cat dander, birch pollen, house dust, mite, grass pollen, etc.) and antigens from pathogens such as viruses, bacteria, fungi and parasites. These antigens may be in the form of whole inactivated organisms, peptides, proteins, glycoproteins, carbohydrates or combinations thereof.

Bioactive agents also includes peptides, proteins, genes, and nucleic acids, such as DNA, RNA, siRNA, etc.

2. Other Agents

Other agents include chromophores, dyes, colorants, lakes, and combinations thereof.

A "chromophore" is broadly defined herein as a substance (solid, liquid, or gas) that has color or imparts a color to the nanoparticles (including when the substance itself lacks color, for example, a clear gas, but scatters electromagnetic waves, for example, light, and thus may appear colored, for example, white, blue, green, or yellow, depending on its scattering properties) under some conditions, for example, all of the time or after exposure to a certain wavelength (such as in a fluorescent substance). For example, a chromophore can be a fluorescent, phosphorescent, wavelength up-converting, or other substance that may normally be substantially invisible, but that emits ultraviolet, visible, or infrared wavelengths during and/or after exposure to wavelengths from a particular region of the electromagnetic spectrum. A chromophore can also be a substance that reversibly or irreversibly changes color spontaneously or in response to any stimulus or photobleaches when exposed to a specific light energy. For example, a chromophore can be a substance that changes appearance or photobleaches upon simultaneous absorption of multiple photons (for example two photon absorption).

As used herein, a substance (such as a chromophore) is "invisible" when essentially no color can be detected (such as in a tissue marking site) apart from the normal coloration of the substance's surroundings (such as skin or other tissue) by the naked eye under normal lighting conditions, for example, diffuse sunlight or standard artificial lighting. A substance is "undetectable" when it is invisible to the naked eye under normal lighting conditions, and also invisible by the naked eye, or a device, under any other lighting conditions (such as fluorescent, UV, or near-infrared).

The dyes can be fluorescent, chemiluminescent, reflective, in the form of amorphous, crystalline, spherical or reflective particles, or may be colorless until activated. The chromophore can be or include rifampin, beta-carotene, tetracycline, indocyanine green, Evan's blue, methylene blue, FD&C Blue No. 1 (Brilliant Blue FCF), FD&C Green No. 3 (Fast Green FCF), FD&C Red No. 3 (Erythrosine), FD&C Red No. 40, FD&C Yellow No. 5 (Tartrazine), FD&C Yellow No. 6 (Sunset Yellow FCF) or other FD&C and D&C dyes and lakes. A lake is a straight color extended on a substratum by adsorption, coprecipitation, or chemical combination that does not include any combination of ingredients made by simple mixing process. The substratum can be alumina, blanc fixe, gloss white, clay, titanium dioxide, zinc oxide, talc, rosin, aluminum benzoate, calcium carbonate, or any combination of two or more of these. The lakes are also salts prepared from one of the straight colors by combining the color with the basic radical sodium, potassium, aluminum, barium, calcium, strontium, or zirconium. In addition, chromophores include natural pigments, metal oxides (such as synthetic iron oxides and titanium dioxide) and carbon. The chromophore can be any colored substance approved by the United States Food and Drug Administration for use in humans. In certain embodiments, the chromophore can be detected by the naked eye under normal lighting conditions or when exposed to UV, near-UV, IR, or near-IR radiation.

Other dyes that can be incorporated into polymer include acid fuchsin, alcian blue, alizarin red s, auramine o, azure a and b, Bismarck brown y, brilliant cresyl blue ald, brilliant green, carmine, cibacron blue 3GA, congo red, cresyl violet acetate, crystal violet, eosin b, eosin y, erythrosin b, fast green fcf, giemsa, hematoylin, indigo carmine, Janus green b, Jenner's stain, malachite green oxalate, methyl blue, methylene blue, methyl green, methyl violet 2b, neutral red, Nile blue a, orange II, orange G, orcein, paraosaniline chloride, phloxine b, pyronin b and y, reactive blue 4 and 72, reactive brown 10, reactive green 5 and 19, reactive red 120, reactive yellow 2,3, 13 and 86, rose bengal, safranin o, Sudan III and IV, Sudan black B and toluidine blue. Examples demonstrate incorporation of water-soluble dyes indigo, indocyanin green, brilliant blue G, and beta-carotene, as well as water-insoluble dye, copper-phthalocyanin.

The agent to be encapsulated may be in liquid, solid, or gas form. However, typically the agent is in liquid or solid form. It may be dissolved in the core polymer solvent or dispersed in the core polymer solvent or any of the other polymer solvents used to form the multi-walled nanoparticles. The agent may be contained in micro- or nanodroplets dispersed in the solvent or may be dispersed as solid micro- or nanoparticles (e.g., micronized or nanonized solids) in the solvent. Alternatively, the agent to be encapsulated can be added to the core polymer solution in the form of an emulsion, such as an oil-in-water emulsion or a cryogenic emulsion.

C. Nanoparticles

Particles having an average particle size of between 10 nm and 10 microns are useful in the compositions described herein In preferred embodiments, the particles are nanoparticles, having a size range from about 10 nm to 1 micron, preferably from about 10 nm to about 0.1 microns. In particularly preferred embodiments, the particles have a size range from about 500 to about 600 nm. The particles can have any shape but are generally spherical in shape.

The compositions described herein contain a monodisperse plurality of nanoparticles. Preferably, the method used to form the nanoparticles produces a monodisperse distribution of nanoparticles; however, methods producing polydisperse nanoparticle distributions can be used. If the method does not produce particles having a monodisperse size distribution, the particles are separated following particle formation to produce a plurality of particles having the desired size range and distribution.

Nanoparticles useful in the compositions described herein can be prepared using any suitable method known in the art. Common microencapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

In certain embodiments, the nanoparticles incorporated in the compositions discussed herein are multi-walled nanoparticles.

Multi-walled nanoparticles useful in the compositions disclosed herein can be prepared, for example, using "sequential phase inversion nanoencapsulation" (sPIN), as disclosed below.

1. Spray Drying

Methods for forming microspheres/nanospheres using spray drying techniques are described in U.S. Pat. No. 6,620,617, to Mathiowitz et al. In this method, the polymer is dissolved in an organic solvent such as methylene chloride or in water. A known amount of one or more active agents to be incorporated in the particles is suspended (in the case of an insoluble active agent) or co-dissolved (in the case of a soluble active agent) in the polymer solution. The solution or dispersion is pumped through a micronizing nozzle driven by a flow of compressed gas, and the resulting aerosol is suspended in a heated cyclone of air, allowing the solvent to evaporate from the microdroplets, forming particles. Microspheres/nanospheres ranging between 0.1-10 microns can be obtained using this method.

2. Interfacial Polymerization

Interfacial polymerization can also be used to encapsulate one or more active agents. Using this method, a monomer and the active agent(s) are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

3. Hot Melt Microencapsulation

Microspheres can be formed from polymers such as polyesters and polyanhydrides using hot melt microencapsulation methods as described in Mathiowitz et al., *Reactive Polymers*, 6:275 (1987). In this method, the use of polymers with molecular weights between 3-75,000 daltons is preferred. In this method, the polymer first is melted and then mixed with the solid particles of one or more active agents to be incorporated that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decanting with petroleum ether to give a free-flowing powder.

4. Phase Separation Microencapsulation

In phase separation microencapsulation techniques, a polymer solution is stirred, optionally in the presence of one or more active agents to be encapsulated. While continuing to uniformly suspend the material through stirring, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

a. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

b. Solvent Evaporation Microencapsulation

Methods for forming microspheres using solvent evaporation techniques are described in E. Mathiowitz et al., *J. Scanning Microscopy*, 4:329 (1990); L. R. Beck et al., *Fertil. Steril.*, 31:545 (1979); L. R. Beck et al *Am J Obstet Gynecol* 135(3) (1979); S. Benita et al., *J. Pharm. Sci.*, 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microspheres/nanospheres. This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

c. Solvent Removal Microencapsulation

The solvent removal microencapsulation technique is primarily designed for polyanhydrides and is described, for example, in WO 93/21906 to Brown University Research Foundation. In this method, the substance to be incorporated is dispersed or dissolved in a solution of the selected polymer in a volatile organic solvent, such as methylene chloride. This mixture is suspended by stirring in an organic oil, such as silicon oil, to form an emulsion. Microspheres that range between 1-300 microns can be obtained by this procedure. Substances which can be incorporated in the microspheres include pharmaceuticals, pesticides, nutrients, imaging agents, and metal compounds.

5. Coacervation

Encapsulation procedures for various substances using coacervation techniques are known in the art, for example, in GB-B-929 406; GB-B-929 40 1; and U.S. Pat. Nos. 3,266, 987, 4,794,000, and 4,460,563. Coacervation involves the separation of a macromolecular solution into two immiscible liquid phases. One phase is a dense coacervate phase, which contains a high concentration of the polymer encapsulant (and optionally one or more active agents), while the second phase contains a low concentration of the polymer. Within the dense coacervate phase, the polymer encapsulant forms nanoscale or microscale droplets. Coacervation may be induced by a temperature change, addition of a non-solvent or addition of a micro-salt (simple coacervation), or by the addition of another polymer thereby forming an interpolymer complex (complex coacervation).

6. Low Temperature Casting of Microspheres

Methods for very low temperature casting of controlled release microspheres are described in U.S. Pat. No. 5,019,400 to Gombotz et al. In this method, a polymer is dissolved in a solvent optionally with one or more dissolved or dispersed active agents. The mixture is then atomized into a vessel containing a liquid non-solvent at a temperature below the freezing point of the polymer-substance solution which freezes the polymer droplets. As the droplets and non-solvent for the polymer are warmed, the solvent in the droplets thaws and is extracted into the non-solvent, resulting in the hardening of the microspheres.

7. Phase Inversion Nanoencapsulation (PIN)

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated with the particles or the particles are dispersed in the polymer. See, e.g., U.S. Pat. No. 6,143,211 to Mathiowitz, et al. The method can be used to produce monodisperse populations of nanoparticles and microparticles in a wide range of sizes, including, for example, about 100 nanometers to about 10 microns.

Advantageously, an emulsion need not be formed prior to precipitation. The process can be used to form microspheres from thermoplastic polymers.

8. Sequential Phase Inversion Nanoencapsulation (sPIN)

Multi-walled nanoparticles can also be formed by a process referred to herein as "sequential phase inversion nanoencapsulation" (sPIN). This process is described in detail below in Section IV. sPIN is particularly suited for forming monodisperse populations of nanoparticles, avoiding the need for an additional separations step to achieve a monodisperse population of nanoparticles.

D. Enteral Dosage Forms

The compositions are preferably in a form suitable for enteral administration, preferably oral administration. Exemplary routes of enteral administration include, but are not limited to, sublingual, buccal, and oral. Suitable dosage forms for enteral administration include, but are not limited to, tablets, capsules, caplets, solutions, suspensions, syrups, powders, or thin films.

The enteral dosage forms can contain one or more excipients including any number of medically or pharmaceutically acceptable excipients such as preservatives, lipids, fatty acids, waxes, surfactants, plasticizers, porosigens, antioxidants, bulking agents, buffering agents, chelating agents, cosolvents, water-soluble agents, insoluble agents, metal cations, anions, salts, osmotic agents, synthetic polymers, biological polymers, hydrophilic polymers, polysaccharides, sugars, hydrophobic polymers, hydrophilic block copolymers, hydrophobic block copolymers, block copolymers containing hydrophilic and hydrophobic blocks. Such excipients can be used singly or in combinations of two or more excipients when preparing nanoparticle compositions. These excipients can be useful in order to alter or affect drug release, water uptake, polymer degradation, stability of the bioactive agent, among other properties.

The one or more excipients can be incorporated during formation of the nanoparticles, for example by addition to one or more of the polymer solutions. Alternatively, the one or more excipients can be combined with the nanoparticles after they are formed, when the nanoparticles are formulated into pharmaceutically acceptable compositions. The one or more excipients can be used at a concentration from about 1% to about 90% by weight of the composition.

Examples of water soluble and hydrophilic excipients include poly(vinyl pyrrolidone) or PVP and copolymers containing one or more blocks of PVP along with blocks of other biocompatible polymers (for example, poly(lactide) or poly (lactide-co-glycolide) or polycaprolactone); poly(ethylene glycol) or PEG and copolymers containing blocks of PEG along with blocks of other biocompatible polymers (for example, poly(lactide) or poly(lactide-co-glycolide) or polycaprolactone); poly(ethylene oxide) or PEO, and copolymers containing one or more blocks of PEO along with blocks of other biocompatible polymers (for example, poly(lactide) or poly(lactide-co-glycolide) or polycaprolactone) as well as block copolymers containing PEO and polypropylene oxide) or PPO such as the triblock copolymers of PEO-PPO-PEO (such as Poloxamers™, Pluronics™); and, modified copolymers of PPO and PEO containing ethylene diamine (Poloxamines™ and Tetronics™).

In one embodiment, the nanoparticles described herein are formulated as a tablet, capsule, or caplet. In one embodiment, the tablet, capsule or caplet can be coated with a modified release coating, such as an enteric coating. Enteric coatings are well known in the art. For example, enteric coatings are available under the trade name Eudragit™. In another embodiment, the particles can be encapsulated in an enteric capsule, wherein the enteric polymer is a component of the capsule shell.

In another embodiment, the nanoparticles can be dispersed in a bioadhesive matrix. For examples, the nanoparticles can be dispersed in a bulk polymer, which itself is bioadhesive. The resulting dispersion can be encapsulated in a capsule, such as a hard or soft gelatin or non-gelatin capsule or formulated as a tablet or caplet. The dosage form can be coated to modify release of the agent as described above.

III. Methods for Increasing the Uptake of Nanoparticles in the Gastrointestinal Tract Also disclosed herein is a method of increasing the intestinal uptake of a composition containing a plurality of nanoparticles, preferably containing one or more active agents. The method includes the step of enterally administering, preferably orally administering, to a patient in need of treatment a composition containing a plurality of nanoparticles, preferably containing one or more agents.

Preferably the population of nanoparticles has a monodisperse size distribution.

The nanoparticles are formed from a polymeric material which has the following characteristics: (1) possesses a higher adhesion to freshly excised rat intestinal tissue, as measured in terms of fracture strength using the assay described in Example 3, than PMMA; (2) exhibits a lower contact angle with rat mucin than PMMA; and (3) when formed into spherical nanoparticles, exhibits a higher binding ratio to the jejunum, as measured by the everted sac method as described in Example 3, than PMMA nanoparticles of substantially equivalent mean particle size.

In preferred embodiments, the nanoparticles are formed from a polymeric material which has the following characteristics: (1) possesses an adhesion to freshly excised rat intestinal tissue, as measured in terms of fracture strength using the assay described in Example 3, that is equivalent to or greater than PS; (2) exhibits a contact angle with rat mucin that is equivalent to or less than the contact angle for PS; and (3) when formed into spherical nanoparticles, exhibits a binding ratio to the jejunum, as measured by the everted sac method as described in Example 3, that is equivalent to or greater than PS nanoparticles of substantially equivalent mean particle size.

The increase in total intestinal uptake can be expressed as a percentage increase in the total intestinal uptake of the composition described above and the total intestinal uptake of the nanoparticles in the same composition, in the absence of the above-described polymeric material. For example, as described in Example 4, PMMA-BMAD nanospheres exhibited a total intestinal uptake of 66.9±12.9% of the administered dose, whereas PMMA nanospheres exhibited a total intestinal uptake of 5.8±1.9% of the administered dose. The percent increase is calculated by dividing the net increase in intestinal uptake (i.e. the percent intestinal uptake of the PMMA-BMAD nanospheres minus the percent intestinal uptake of the PMMA nanospheres) by the intestinal uptake of the nanoparticles in the same composition, in the absence of the above-described polymeric material (i.e. the percent intestinal uptake of the PMMA nanospheres), and multiplying by 100. Accordingly, the increase in total intestinal uptake upon inclusion of BMAD in the composition is calculated to be at least 600%.

In preferred embodiments, the total intestinal uptake of the nanoparticles in the composition is increased by more than 20%, 30%, 40%, 50%, 75%, 100%, 125%, 150%, 175%, 200%, 225%, 250%, 275%, 300%, 325%, 350%, 375%, 400%, 450%, 500%, 550%, 600%, 650%, 700%, 750%, 800%, 850%, 900%, 950%, or 1000%, as compared to the total intestinal uptake of the nanoparticles in the same composition in the absence of the above-described polymeric material, as measured using the in vivo isolated loop assay described in Example 4. In particularly preferred embodiments, the total intestinal uptake of a plurality of nanoparticles in the composition is increased by more than 500% compared to the total intestinal uptake of a plurality of nanoparticles in the same composition without the polymeric material, as measured using the in vivo isolated loop assay described in Example 4.

In some of the embodiments, the polymeric material exhibits adhesion to freshly excised rat intestinal tissue, as measured in terms of fracture strength using the assay described in Example 3, of greater than 100, 110, 120, 130, 140, 150, 160, 170, 180, 190, 200, 210, 220, 230, 240, or 250 mN/cm². In particularly preferred embodiments, the polymeric material exhibits adhesion to freshly excised rat intestinal tissue, as measured in terms of fracture strength using the assay described in Example 3, of greater than 110 mN/cm², more preferably greater than 150 mN/cm², most preferably greater than 200 mN/cm².

In some of the methods described above, the polymeric material exhibits a contact angle with rat mucin of less than 50, 45, 40, 39, 38, 37, 36, 35, 34, 33, 32, 31, 30, 29, 28, 27, 26, 25, 24, 23, 22, 21, or 20°. In preferred embodiments, the polymeric material exhibits a contact angle with rat mucin of less than 40°, more preferably less than 37°, more preferably less than 35°, more preferably less than 32°, and most preferably less than 30°.

In some of the methods described above, the polymeric material, when formed into spherical nanoparticles, exhibits a binding ratio to the jejunum, as measured by the everted sac method as described in Example 3, of greater than 1.5, 1.75, 2.0, 2.25, 2.5, 2.75, 3.0, 3.25, 3.5, 3.75, or 4.0. In preferred embodiments, the polymeric material, when formed into spherical nanoparticles, exhibits a binding ratio to the jejunum, as measured by the everted sac method as described in Example 3, of greater than 1.75, more preferably greater than 2.0, more preferably greater than 2.5, most preferably greater than 3.0.

In order to achieve effective release of the drug at the optimal location in the gastrointestinal tract following oral administration, typically a coordinated combination of controlled release and bioadhesive elements in the nanoparticles, or a composition containing the nanoparticles, is used to achieve release in the desired region where enhanced uptake occurs due to the inclusion of the bioadhesive elements.

In a normal human adult male, the gastrointestinal (GI) tract is approximately 25 feet long and consists of the following components: 1) mouth (buccal cavity; includes salivary glands, mucosa, teeth and tongue); 2) pharynx; 3) esophagus and cardia; 4) stomach, which includes the antrum and pylorus; 5) intestine, including the small intestine, which has three parts-duodenum, jejunum, and ileum, and the large intestine, which also has three parts-cecum, colon (ascending colon, transverse colon, descending colon and sigmoid flexure) and rectum; and 6) the anus. Under normal circumstances, a drug may be expected to remain in the stomach for 2 to 4 hours (gastric emptying time) and in the small intestine for 4 to 10 hours, although there is a substantial variation between people, and even in the same person on different occasions.

The gastric emptying time for a dosage form is most rapid with a fasting stomach, becoming slower as the food content is increased. Changes in gastric emptying time and/or intestinal motility can affect dosage form transit time and thus the opportunity for drug dissolution and absorption. Generally drugs are better absorbed in the small intestine (because of the larger surface area) than in the stomach, therefore quicker stomach emptying will increase drug absorption. Generally, the quicker the stomach emptying (shorter stomach emptying time), the higher the plasma concentration. Further, slower stomach emptying can cause increased degradation of drugs in the stomach's lower pH. Food can affect the rate of gastric emptying. For example fatty food can slow gastric emptying and retard drug absorption. Generally the extent of absorption is not greatly reduced. Occasionally absorption may be improved.

The various gastrointestinal regions and typical transit times are shown in Table 1.

TABLE 1

Characteristics of Gastro-intestinal Physiology

| REGION | pH | Membrane | Blood Supply | Surface Area | Transit Time | Bypass liver |
|---|---|---|---|---|---|---|
| Buccal | approx 6 | thin | Good, fast absorption with low dose | small | Short, unless controlled | yes |
| Esophagus | 6 | Very thick no absorption | — | small | short | — |
| Stomach | 1-3 decomposition, weak acid unionized | normal | good | small | 30-40 min, reduced absorption | no |
| Duodenum | 4-5.5 bile duct, surfactant properties | normal | good | very large | very short (6" long), window effect | no |
| Small Intestine | 6-7 | normal | good | very large 10-14 ft, 80 cm$^2$/cm | about 3 hr | no |
| Large Intestine | 6.8-7 | — | good | not very large 4-5 ft | long, up to 24 hr | lower colon, rectum yes |

IV. Methods for Preparing Multi-Walled Nanoparticles

Also disclosed herein are methods for making multi-walled nanoparticles, referred to herein as "sequential phase inversion nanoencapsulation" (sPIN).

In sPIN, a core polymer is dissolved in a first solvent. If an agent is to be encapsulated, the active agent is dissolved or dispersed in a core polymer solvent. The core polymer, core polymer solvent, and optional agent to be encapsulated form a mixture having a continuous phase, in which the core polymer solvent is the continuous phase. The shell polymer is dissolved in a shell polymer solvent, which is a non-solvent for the core polymer. The solutions of the core polymer and shell polymer are mixed together. The resulting decreases the solubility of the core polymer at its cloud point due to the presence of the shell polymer solvent results in the preferential phase separation of the core polymer and, optionally, encapsulation of the agent. When a non-solvent for the core polymer and the shell polymer is added to this unstable mixture, the shell polymer engulfs the core polymer as phase inversion is completed to form a double-walled nanoparticle.

The methods described herein provide a one-step procedure for the preparation of multi-walled particles, such as double-walled nanoparticles, which is nearly instantaneous, and does not require emulsification of the solvent.

The procedure described above with respect to double-walled nanoparticles can be modified to form multi-walled nanoparticles having three or more layers. The number of walls is dependent on identifying suitable polymer-solvent pairs. For example, to form a triple-walled nanoparticle, a core polymer is dissolved in a core polymer solvent to form a core polymer solution, where the core polymer solvent is a solvent for the core polymer, a second polymer and the shell polymer. The second polymer is dissolved in a polymer solvent to form a second polymer solution, where the second polymer solvent is a solvent for the second polymer but is not a solvent for the core polymer. The shell polymer is dissolved in a shell polymer solvent to form a shell polymer solution, where the shell polymer solvent is a solvent for the shell polymer, but is not a solvent for the core polymer or the second polymer.

The core polymer solution is added to the second polymer solution, optionally in the presence of an agent to be encapsulated. The resulting decrease in the solubility of the core polymer due to the presence of the second polymer solvent results in the preferential phase separation of the core polymer and, if desired, encapsulation of the agent. Then the shell polymer solution is added to this mixture. The resulting decrease in the solubility of the second polymer due to the presence of the shell polymer solvent results in the preferential phase separation of the second polymer which encapsulates the core polymer. Finally, a non-solvent for the core polymer, second polymer, and shell polymer can be added to this mixture. The resulting decrease in the solubility of the shell polymer due to the presence of the non-solvent results in the preferential phase separation of the shell polymer thereby forming triple-walled nanoparticles.

An alternative method for forming multi-walled nanoparticles having three or more layers involves adding the non-solvent after the second polymer solution is mixed with the core polymer solution. In this embodiment, the core polymer solution, second polymer solution and shell solution are formed as described above. Then the core polymer solution and second polymer solution are mixed. Next the non-solvent is added, thereby forming double-walled nanoparticles in the solvent-non-solvent mixture. Finally, the third polymer solution is added to this mixture, to form triple-walled nanoparticles.

The above-described method can be further modified by selecting appropriate solvents for the polymers and a non-solvent for all of the polymers, as described above with respect to double- and triple-walled nanoparticles, to include additional walls in the multi-walled nanoparticles.

In one embodiment, the multi-walled nanoparticles can be formed in the absence of a non-solvent, and/or where the second polymer solvent is the same as the core polymer solvent. For example, precipitation of the core polymer can be controlled by change in temperature of the operating conditions. Alternatively precipitation of one of the polymers can be controlled by the addition of one or more excipients that act as precipitating agents for the core polymer, second polymer, and/or shell polymer. The precipitating agent depends on the polymers and solvents used. Exemplary agents include salts.

A. Core Polymer and Core Polymer Solvent a. Core Polymer Solvent

For the multi-walled nanoparticles, the core polymer is dissolved in a core polymer solvent. The core polymer solvent is selected so that both the core polymer and the polymer used to form the next wall in a multi-walled nanoparticle are soluble, i.e. either the core polymer, in double-walled nanoparticles, or a second polymer, in nanoparticles containing three or more walls. For example, with respect to forming double-walled nanoparticles, both the core polymer and the shell polymer are generally soluble in the core polymer solvent at the operating conditions. In one embodiment, the operating conditions are standard temperature (25° C.) and pressure (1 atm), however, other temperatures may be appropriate based on the polymer-solvent pair, such as 40° C. to 60° C.

The solvent is any suitable solvent for dissolving both the core polymer and the polymer used to form the next wall in the multi-walled nanoparticles. Typically the solvent will be a common organic solvent, such as a halogenated aliphatic hydrocarbon such as methylene chloride, chloroform and the like; an alcohol; an aromatic hydrocarbon such as toluene; a halogenated aromatic hydrocarbon; an ether such as methyl t-butyl; a cyclic ether such as tetrahydrofuran; ethyl acetate; diethylcarbonate; acetone; or cyclohexane. If an agent is being encapsulated in the multi-walled nanoparticles, preferably the core polymer solvent is inert with respect to the agent to be encapsulated and with respect to the polymer.

Additives, such as surfactants, can be used to alter polymer morphology and/or particle size. Suitable surfactants include anionic, cationic, amphoteric, and non-ionic surfactants.

Anionic surfactants include, but are not limited to, di-(2 ethylhexyl) sodium sulfosuccinate.

Non-ionic surfactants include, but are not limited to, the fatty acids and the esters thereof; surfactants in the amphoteric group include (1) substances classified as simple, conjugated and derived proteins such as the albumins, gelatins, and glycoproteins, and (2) substances contained within the phospholipid classification, for example lecithins.

The amine salts and the quaternary ammonium salts within the cationic group are also useful surfactants. Other surfactant compounds include polysaccharides and their derivatives, the mucopolysaccharides and the polysorbates and their derivatives. Synthetic polymers that may be used as surfactants include compositions such as polyethylene glycol and polypropylene glycol. Further examples of suitable surfactants include glycoproteins, glycolipids, galactose, gelatins, modified fluid gelatins and galacturonic acid.

Hydrophobic surfactants include, but are not limited to, fatty acids and cholesterol. Examples of fatty acids include butyric acid, valeric acid, caproic acid, enanthic acid, caprylic acid, pelargonic acid, caprylic acid, undecylic acid, lauric acid, tridecylic acid, myristic acid, pentadecylic acid, palmitic acid, heptadecylic acid, stearic acid, nonadecanoic acid, arachic acid, isocrotonic acid, undecylenic acid, oleic acid, elaidic acid, sorbic acid, linoleic acid, linolenic acid and arachidonic acid.

Hydrophilic surfactants include, but are not limited to, amphiphilic solvents like TWEEN® 20 and polyvinyl alcohol.

b. Core Polymer

The core polymer may be any suitable nanoencapsulation material including, but not limited to, non-biodegradable and biodegradable polymers. Biodegradable polymers can be used as the core polymer for drug delivery applications, wherein one or more encapsulated active agents are released over time as the core polymer degrades. Alternatively, the core polymer can be a non-biodegradable polymer. Suitable applications for non-biodegradable core polymers include bioimaging, which requires that the imaging agent remain encapsulated within the nanoparticles in order to accurately provide the location of the nanoparticles.

Suitable polymers for the core polymer include, but are not limited to, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly (hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers.

In one embodiment, the core polymer is a biodegradable polyester or polyanhydride. In a particular embodiment, the polyester is copolymer of lactic acid and glycolic acid.

Examples of preferred non-biodegradable polymers include ethylene vinyl acetate, poly(meth) acrylic acid, polyamides, copolymers and mixtures thereof.

Excipients may also be added to the core polymer to alter its porosity, permeability, and or degradation profile. For example, excipients can be added to modulate release of the agent from the core polymer. Suitable excipients may include, but are not limited to, inorganic and organic materials such as sucrose, hydroxypropyl cellulose, sodium chloride, sodium chloride, xylitol, sorbitol, lactose, dextrose, maltodextrins and dextrates.

Excipients may also be added to the core polymer to alter its hydration and disintegration properties. Suitable pH dependent enteric excipients may include, but are not limited to, cellulose acetate phthalate, acdisol, hydroxypropyl cellulose, and hydroxypropyl methyl cellulose.

c. Core Polymer Solution

The molecular weight range for the core polymer in the core polymer solution ranges from about 1 kDa to about 150,000 kDa, preferably from about 2 kDa to about 200 kDa, more preferably from about 2 kDa to about 150 kDa, most preferably from about 2 kDa to about 100 kDa. Suitable core polymer concentrations in the core polymer solution range from about 0.01 to about 50% (weight/volume), depending primarily upon the molecular weight of the core polymer and the resulting viscosity of the core polymer solution. In general, the low molecular weight polymers permit usage of higher polymer concentrations. The preferred concentration range is on the order of about 0.1% to about 10% (weight/volume), while the preferred core polymer concentration typically will be about 5% (weight/volume) or lower. It has been found that polymer concentrations ranging from about 1% to about 5% (weight/volume) are particularly useful for the methods described herein.

The viscosity of the core polymer solution preferably is less than about 3.5 centipoise and more preferably less than about 2 centipoise, although higher viscosities such as about 4 or even about 6 centipoise are possible depending upon adjustment of other parameters such as molecular weight.

It will be appreciated by those of ordinary skill in the art that polymer concentration, polymer molecular weight and viscosity are interrelated, and that varying one will likely affect the others.

B. Agents to be Encapsulated

Any agent can be encapsulated in the core polymer. Suitable agents include, but are not limited to, the agents listed above in Section II. B.

The loading range for the agent within the nanoparticles is from about 0.01 to about 80% (agent weight/polymer weight), preferably from 0.01% to about 50% (wt/wt), more preferably from about 0.01% to about 25% (wt/wt), even more preferably from about 0.01% to about 10% (wt/wt), most preferably from about 0.1% to about 5% (wt/wt). For small molecules, the percent loading is typically from about 0.01% to about 20% (wt/wt), although higher loadings may be achieved for cores containing agent alone without polymer and/or for hydrophobic drugs and/or insoluble metals.

For large biomolecules, such as proteins and nucleic acids, typical loadings are from about 0.01% to about 5% (wt/wt), preferably from about 0.01% to about 2.5% (wt/wt), more preferably from about 0.01% to about 1% (wt/wt).

C. Second Polymer, Shell Polymer and Shell Polymer Solvent

The second polymer can be any of the polymers described above with respect to the core polymer. However, the second polymer is a different than the core polymer. In one embodiment, the second polymer is a biodegradable, non-bioadhesive polymer. In another embodiment, the shell polymer is a non-degradable, non-bioadhesive polymer. In still another embodiment, the shell polymer is a bioadhesive polymer, preferably a biodegradable, bioadhesive polymer.

In double walled nanoparticles, the second polymer is the shell polymer. However, in nanoparticles containing three or more polymers, the second polymer is not the shell polymer. Rather the shell polymer is the final polymer added to form the multi-walled nanoparticles.

In nanoparticles containing more than three walls, a third, fourth, etc. polymer are included in forming the nanoparticles. Like the second polymer, these subsequently added polymers polymer can be any of the polymers described above with respect to the core polymer. However, they are different polymers than the core polymer and the polymers in the preceding layers.

a. Shell Polymer

For drug delivery applications, the shell polymer is preferably a biodegradable polymer, such as those described above for the core polymer. The shell polymer can prevent burst release of the agent by preventing release of the agent that is on the surface of the core. In one embodiment the shell polymer is bioadhesive. Alternatively, the outermost wall of the multi-walled nanoparticles may contain a bioadhesive coating or a matrix coating.

Triple-walled particles containing a biodegradable core and a second biodegradable polymer layer can further contain a bioadhesive shell which adheres the particles to the mucosa at the desired site of release in the gastrointestinal tract. Alternatively, double-walled particles containing a biodegradable core and a biodegradable shell can be dispersed in a bioadhesives matrix. Suitable bioadhesives materials are described below.

The molecular weight range for the shell polymer ranges from about 1 kDa to about 150,000 kDa, preferably from about 2 kDa to about 50 kDa.

Excipients may also be added to the shell polymer to alter its porosity and permeability. Suitable excipients may include inorganic and organic materials such as sucrose, hydroxypropyl cellulose, sodium chloride, sodium chloride, xylitol, sorbitol, lactose, dextrose, maltodextrins and dextrates Excipients may also be added to the shell polymer to alter its hydration and disintegration properties. Suitable pH dependent enteric excipients may include cellulose acetate phthalate, acdisol, hydroxypropyl cellulose, and hydroxypropyl methyl cellulose.

b. Second or Shell Polymer Solvent

The second polymer is dissolved in a second polymer solvent in which the core polymer and any other polymer used to form the one or more walls in the multi-walled nanoparticles is insoluble, to form a second polymer solution. Suitable solvents include, but are not limited to, halogenated aliphatic hydrocarbon such as methylene chloride, chloroform and the like; an alcohol; an aromatic hydrocarbon such as toluene; a halogenated aromatic hydrocarbon; an ether such as methyl t-butyl; a cyclic ether such as tetrahydrofuran; ethyl acetate; diethylcarbonate; acetone; or cyclohexane. The solvents may be used alone or in combination. All solvents must be miscible. Surfactants, such as those described above for the core polymer, may be added to alter the polymer morphology and/or polymer solubility of the shell polymer, and/or the particle size of the nanoparticles.

Appropriate solvents are similarly selected for the third, fourth, etc. polymers, if included in forming the multi-walled nanoparticles. Thus, for a third polymer, the third polymer is dissolved in a third polymer solvent in which the core polymer and any other polymer used to form the one or more walls in the multi-walled nanoparticles are insoluble, forming a third polymer solution.

If the second polymer is the shell polymer, the second polymer solvent is generally referred to as the "shell polymer solvent", and is used to form a "shell polymer solution".

c. Second or Shell Polymer Solution

Suitable second polymer concentrations in the second polymer solution range from about 0.01 to about 50% (weight/volume), depending primarily upon the molecular weight of the shell polymer and the resulting viscosity of the second polymer solution. In general, the low molecular weight polymers permit usage of higher polymer concentrations. The preferred concentration range is on the order of about 0.1% to about 10% (weight/volume), while the preferred polymer concentration typically will be about 5% (weight/volume) or lower. It has been found that polymer concentrations ranging from about 1% to about 5% (weight/volume) are particularly useful for the methods described herein.

The viscosity of the second polymer solution preferably is less than about 3.5 centipoise and more preferably less than about 2 centipoise, although higher viscosities such as about 4 or even about 6 centipoise are possible depending upon adjustment of other parameters such as molecular weight. It will be appreciated by those of ordinary skill in the art that polymer concentration, polymer molecular weight and viscosity are interrelated, and that varying one will likely affect the others.

1. Bioadhesive Polymers

Particularly preferred polymers for the shell polymer are bioadhesive polymers. A bioadhesive polymer is one that binds to mucosal epithelium under normal physiological conditions. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., van der Waals interactions) and stronger specific interactions, which include hydrogen bonds. The hydrophilic functional groups primarily responsible for forming hydrogen bonds are the hydroxyl and the carboxylic groups.

Bioadhesives with varying hydration times and durations of bioadhesiveness in aqueous media could directly impact the performance of oral formulations. Bioadhesives have demonstrated the ability to promote intimate contact with the GI mucosa for prolonged periods of time leading to increased bioavailability of small molecule drugs. Additionally, it has been reported that a relationship exists between increased bioadhesiveness and increased nanoparticle uptake. Given the therapeutic aims of the oral formulation, taking into account the pharmacokinetics of the release and mucus turnover, choosing a polymer that will remain bioadhesive for the desired duration is of great importance to the field of oral drug delivery.

For example, to achieve prolonged release in the intestines of a small molecule over the period of hours, a bioadhesive with a low rate of hydration might be ideal, e.g. poly(fumaric-co-sebacic anhydride). However, as a carrier to enhance nanoparticle uptake, the bioadhesive polymer may function to promote contact between the nanoparticle and the GI mucosa for a short time until the nanoparticle can achieve mucus permeation and then dissolve prior to nanoparticle uptake.

Representative bioadhesive polymers include bioerodible hydrogels, such as those described by Sawhney, et al., in *Macromolecules,* 1993, 26:581-587, the teachings of which are incorporated herein by reference. Other suitable bioadhesive polymers are described in U.S. Pat. No. 6,235,313 to Mathiowitz et al., the teachings of which are incorporated herein by reference, and include polyhydroxy acids, such as poly(lactic acid), polystyrene, polyhyaluronic acids, casein, gelatin, glutin, polyanhydrides, polyacrylic acid, alginate, chitosan; polyacrylates, such as poly(methyl methacrylates), poly(ethyl methacrylates), poly butylmethacrylate), poly (isobutylmethacrylate), poly(hexlmethacrylate), poly(isodecl methacrylate), poly(lauryl methacrylate), poly(phenyl methacrylate), poly(methyl acrylate), poly(isopropyl acrylate), poly(isobutyl acrylate), and poly(octadecl acrylate); polyacrylamides; poly(fumaric-co-sebacic)acid, poly(bis carboxy phenoxy propane-co-sebacic anhydride), polyorthoesters, and combinations thereof.

Suitable polyanhydrides include polyadipic anhydride ("p (AA)"), polyfumaric anhydride, polysebacic anhydride, polymaleic anhydride, polymalic anhydride, polyphthalic anhydride, polyisophthalic anhydride, polyaspartic anhydride, polyterephthalic anhydride, polyisophthalic anhydride, poly carboxyphenoxypropane anhydride and copolymers with other polyanhydrides at different mole ratios.

Optionally, the shell polymer is a blend of hydrophilic polymers and bioadhesive hydrophobic polymers. Suitable hydrophilic polymers include, but are not limited to, hydroxypropylmethylcellulose, hydroxypropylcellulose, carboxymethylcellulose, polyvinylalcohols, polyvinylpyrrolidones, and polyethylene glycols. The hydrophobic polymer may contain gastrosoluble polymers that dissolve in stomach contents, such as Eudragit® E100. The hydrophobic polymer may contain entero-soluble materials that dissolve in the intestine above pH 4.5, such as Eudragit® L-100, Eudragit® S-100, cellulose acetate phthalate, hydroxypropyl methylcellulose phthalate, hydroxypropyl methylcellulose acetate succinate, Eastacryl® 30D dispersion from Eastman Chemicals., Sureteric® (polyvinyl acetate phthalate) and Acryl Eze®.

i. Polymer Containing Hydroxyl Aromatic Moieties

In one embodiment, the bioadhesive material is a polymer containing a plurality of aromatic groups containing one or more hydroxyl groups. Such polymers are described in detail in U.S. Patent Application Publication No. 2005/0201974 to Schestopol, et al., the disclosure of which is incorporated herein by reference. Suitable aromatic moieties include, but are not limited to, catechol and derivatives thereof, trihydroxy aromatic compounds, or polyhydroxy aromatic moieties. In one embodiment, the aromatic moiety is 3,4-dihydroxyphenylalanine (DOPA), tyrosine, or phenylalanine, all of which contain a primary amine. In a preferred embodiment, the aromatic compound is 3,4-dihydroxyphenylalanine.

The degree of substitution by the aromatic moiety can vary based on the desired adhesive strength; it may be as low as 10%, 20%, 25%, 50%, or up to 100% substitution. On average at least 50% of the monomers in the polymeric backbone are substituted with the at least one aromatic moiety. Preferably, 75-95% of the monomers in the backbone are substituted with at least one of the aromatic groups or a side chain containing one or more aromatic groups. In the preferred embodiment, on average 100% of the monomers in the polymeric backbone are substituted with at least one of the aromatic groups or a side chain containing one or more of the aromatic groups.

The bioadhesive polymer can be formed by first coupling the aromatic compound to a monomer or monomers and polymerizing the monomer or monomers to form the bioadhesive polymer. In this embodiment, the monomers may be polymerized to form any polymer, including biodegradable and non-biodegradable polymers. Alternatively, polymer backbones can be modified by covalently attaching the aromatic moieties to the polymer back bone. In those embodiments where the aromatic moieties are grafted to a polymer chain, the aromatic moieties can be part of a compound, side chain oligomer, and/or polymer.

Regardless of the mechanism, the monomer or polymer must contain one or more reactive functional groups which can react with the aromatic moiety to form a covalent bond. In one embodiment, the aromatic moiety contains an amino group and the monomer or polymer contains one or more amino reactive groups. Suitable amino reactive groups include, but are not limited to, aldehydes, ketones, carboxylic acid derivatives, cyclic anhydrides, alkyl halides, acyl azides, isocyanates, isothiocyanates, and succinimidyl esters.

The polymer that forms that backbone of the bioadhesive material containing the aromatic groups may be any non-biodegradable or biodegradable polymer. In the preferred embodiment, the polymer is a hydrophobic polymer. In one embodiment, the polymer is a biodegradable polymer.

Suitable polymer backbones include, but are not limited to, polyanhydrides, polyamides, polycarbonates, polyalkylenes, polyalkylene oxides such as polyethylene glycol, polyalkylene terepthalates such as poly(ethylene terephthalate), polyvinyl alcohols, polyvinyl ethers, polyvinyl esters, polyethylene, polypropylene, poly(vinyl acetate), poly vinyl chloride, polystyrene, polyvinyl halides, polyvinylpyrrolidone, polyhydroxy acids, polysiloxanes, polyurethanes and copolymers thereof, modified celluloses, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, and polyacrylates such as poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate).

Examples of preferred biodegradable polymers for forming the shell polymer include synthetic polymers such as poly hydroxy acids, such as polymers of lactic acid and glycolic acid, polyanhydrides, poly(ortho)esters, polyesters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In one embodiment, the shell polymer is a copolymer of maleic anhydride and butadiene containing DOPA, tyrosine, and/or phenyl alanine groups. In another embodiment, the polymer is a copolymer of maleic anhydride and ethylene containing DOPA, tyrosine, and/or phenyl alanine groups. Other suitable monomers that can be copolymerized with maleic anhydride include vinyl acetate and styrene.

The polymer may be also a known bioadhesive polymer that is hydrophilic or hydrophobic. Hydrophilic polymers include CARBOPOL™ (a high molecular weight, crosslinked, acrylic acid-based polymers manufactured by NOVEON™), polycarbophil, cellulose esters, and dextran.

In some embodiments, one can use non-biodegradable polymers, especially hydrophobic polymers. Examples of preferred non-biodegradable polymers include ethylene vinyl acetate, poly(meth) acrylic acid, copolymers of maleic anhydride with other unsaturated polymerizable monomers, poly(butadiene maleic anhydride), polyamides, copolymers and mixtures thereof, and dextran, cellulose and derivatives thereof.

2. Bioadhesive Oligomers

Shell polymers with enhanced bioadhesive properties can be provided wherein bioadhesive monomers or oligomers, such as anhydride monomers or oligomers, are incorporated into the polymer. The oligomer excipients can be blended or incorporated into a wide range of hydrophilic and hydrophobic polymers including proteins, polysaccharides and synthetic biocompatible polymers Anhydride oligomers may be combined with metal oxide particles to improve bioadhesion even more than with the organic additives alone. The incorporation of oligomer compounds into a wide range of different polymers which are not normally bioadhesive can dramatically increases their adherence to tissue surfaces, such as mucosal membranes.

As used herein, the term "anhydride oligomer" refers to a diacid or polydiacids linked by anhydride bonds, and having carboxy end groups linked to a monoacid such as acetic acid by anhydride bonds. The anhydride oligomers have a molecular weight less than about 5000, typically between about 100 and 5000 Da, or are defined as including between one to about 20 diacid units linked by anhydride bonds. In one embodiment, the diacids are those normally found in the Krebs glycolysis cycle. The anhydride oligomer compounds have high chemical reactivity.

The oligomers can be formed in a reflux reaction of the diacid with excess acetic anhydride. The excess acetic anhydride is evaporated under vacuum, and the resulting oligomer, which is a mixture of species which include between about one to twenty diacid units linked by anhydride bonds, is purified by recrystallizing, for example from toluene or other organic solvents. The oligomer is collected by filtration, and washed, for example, in ethers. The reaction produces anhydride oligomers of mono and poly acids with terminal carboxylic acid groups linked to each other by anhydride linkages.

The anhydride oligomer may be hydrolytically labile. As analyzed by gel permeation chromatography, the molecular weight may be, for example, on the order of 200 to 400 for fumaric acid oligomer (FAPP) and 2000 to 4000 for sebacic acid oligomer (SAPP). The anhydride bonds can be detected by Fourier transform infrared spectroscopy by the characteristic double peak at 1750 cm 1 and 1820 cm 1, with a corresponding disappearance of the carboxylic acid peak normally at 1700 cm 1.

In one embodiment, the oligomers may be made from diacids described for example in U.S. Pat. No. 4,757,128 to Domb et al., U.S. Pat. No. 4,997,904 to Domb, and U.S. Pat. No. 5,175,235 to Domb et al., the disclosures of which are incorporated herein by reference. For example, monomers such as sebacic acid, bis(p carboxy phenoxy)propane, isophathalic acid, fumaric acid, maleic acid, adipic acid or dodecanedioic acid may be used.

3. Bioadhesive Additives

Additives can be added to the shell polymer to alter the properties of the shell polymer provided the additives do not adversely affect the formation of the nanoparticles. Suitable additives include, but are not limited to, dyes and excipients which alter porosity, permeability, hydration, and/or disintegration properties.

Organic dyes because of their electronic charge and hydrophobicity/hydrophilicity can be used to either increase or decrease the bioadhesive properties of polymers when incorporated into the shell polymer. Suitable dyes include, but are not limited to, acid fuchsin, alcian blue, alizarin red s, auramine o, azure a and b, Bismarck brown y, brilliant cresyl blue ald, brilliant green, carmine, cibacron blue 3GA, congo red, cresyl violet acetate, crystal violet, eosin b, eosin y, erythrosin b, fast green fcf, giemsa, hematoylin, indigo carmine, Janus green b, Jenner's stain, malachite green oxalate, methyl blue, methylene blue, methyl green, methyl violet 2b, neutral red, Nile blue a, orange II, orange G, orcein, paraosaniline chloride, phloxine b, pyronin b and y, reactive blue 4 and 72, reactive brown 10, reactive green 5 and 19, reactive red 120, reactive yellow 2,3, 13 and 86, rose bengal, safranin o, Sudan III and IV, Sudan black B and toluidine blue.

The bioadhesives properties can also be improved by adding metal compounds, such as water-insoluble metal oxides and metal hydroxides, which are capable of becoming incorporated into and associated with a polymer to thereby improve the bioadhesiveness of the polymer as described in U.S. Pat. No. 5,985,312, which is incorporated herein by reference in its entirety. As defined herein, a water-insoluble metal compound is defined as a metal compound with little or no solubility in water, for example, less than about 0.0-0.9 mg/ml.

The water-insoluble metal compounds, such as metal oxides, can be incorporated by one of the following mechanisms: (a) physical mixtures which result in entrapment of the metal compound; (b) ionic interaction between metal compound and polymer; (c) surface modification of the polymers which would result in exposed metal compound on the surface; and (d) coating techniques such as fluidized bead, pan coating or any similar methods known to those skilled in the art, which produce a metal compound enriched layer on the surface of the device.

The water-insoluble metal compounds can be derived from metals including calcium, iron, copper, zinc, cadmium, zirconium and titanium. For example, a variety of water-insoluble metal oxide powders may be used to improve the bioadhesive properties of polymers such as ferric oxide, zinc oxide, titanium oxide, copper oxide, barium hydroxide, stannic oxide, aluminum oxide, nickel oxide, zirconium oxide and cadmium oxide. The incorporation of water-insoluble metal compounds such as ferric oxide, copper oxide and zinc oxide can tremendously improve adhesion of the polymer to tissue surfaces such as mucosal membranes, for example in the gastrointestinal system. The polymers incorporating a metal compound thus can be used to form or coat the particles to improve their bioadhesive properties.

D. Non-Solvent

A non-solvent is added to the mixture of polymer solutions, as described above, where the non-solvent is a non-solvent for the polymers used to form the multi-walled nanoparticles. For example, with respect to double walled nanoparticles, a non-solvent is added to the mixture of the core polymer solution and the shell polymer solution, where the non-solvent is a non-solvent for both the core polymer and the shell polymer. The nonsolvent is selected based upon its miscibility in the solvents that form the polymer solutions. Thus, the polymer solvents (e.g., the core polymer solvent and the shell polymer solvent) and nonsolvent are thought of as "pairs".

In one embodiment, the solubility parameter ($\delta(cal/cm^3)^{1/2}$) is a useful indicator of the suitability of the solvent mixture/nonsolvent pairs. The solvent mixture refers to the solvents used in the polymer solutions that are mixed together prior to the addition of the non-solvent.

In some embodiments, the solubility parameter can be a predictor of the miscibility of two solvents and, generally, higher values indicate a more hydrophilic liquid while lower values represent a more hydrophobic liquid (e.g., $\delta i$ water=23.4 $(cal/cm^3)^{1/2}$ whereas $\delta i$hexane=7.3 $(cal/cm^3)^{1/2}$).

In one embodiment, solvent/nonsolvent pairs may be useful where $0 < |\delta$ solvent mixture$-\delta$ nonsolvent$|6$ $(cal/cm^3)^{1/2}$, where $\delta$ solvent mixture is $\delta$ for the mixture of the solvents used to form the polymer solutions that are mixed prior to the addition of the non-solvent. For example, in the formation of double-walled polymers, $\delta$ solvent mixture is the $\delta$ for the mixture of the shell polymer solvent and the core polymer solvent.

Although not wishing to be bound by any theory, an interpretation of this finding is that miscibility of the solvent and the nonsolvent is important for formation of precipitation nuclei which ultimately serve as foci for particle growth. If the mixture of polymer solutions is totally immiscibile in the nonsolvent, then solvent extraction does not occur and nanoparticles are not formed. An intermediate case would involve a solvent mixture/nonsolvent pair with slight miscibility, in which the rate of solvent removal would not be quick enough to form discreet nanoparticles, resulting in aggregation of coalescence of the particles.

The solvent:nonsolvent volume ratio may facilitate determining whether nanoparticles form without particle aggregation or coalescence. A suitable range for solvent mixture:nonsolvent volume ratio is believed to be 1:5-1:1,000,000. Preferably the volume ratios for solvent mixture:nonsolvent range from 1:5 to 1:200 (volume per volume), 1:10 to 1:200, more preferably from 1:5 to 1:100, 1:10 to 1:100.

E. Particle Size

Particles in the range of 10 nm to 10 µm have been produced according to the methods for forming multi-walled particles described herein. Using initial polymer concentrations in the range of 1-2% (weight/volume) with a core polymer solvent such as tetrahydrofuran, a shell polymer solvent, such as ethanol, and a non-solvent, such as petroleum ether, at a volume ratio of 1:75 solvent mixture:non-solvent, generates particles with a diameter of about 500 nm to about 600 nm.

Laser particle size distribution of these nanoparticles revealed a biphasic distribution of particle sizes with peaks at 545 nm and 1668 nm. Scanning electron microscopy (SEM) was used to visualize the nanoparticles. SEM confirmed that the majority of the nanoparticles have a diameter of about 500 nm. In contrast to the results from laser particle size analysis, the particles appear to be fairly monodisperse but with a tendency to aggregate due to the bioadhesiveness of the shell polymer, poly(butadiene maleic anhydride-co-L-dopamine) (pBMAD).

Using very low molecular weight polymers (less than 5 kDa), the viscosity of the initial polymer solution may be low enough to enable the use of higher than 10% (weight/volume) initial polymer concentrations which generally result in nanoparticles. In general, it is likely that at polymer solution concentrations of 15% (weight/volume) and polymer solution viscosities greater than about 3.5 centipoise discreet nanoparticles will not form but, instead, will irreversibly coalesce into intricate, interconnecting fibrilar networks with micron thickness dimensions.

It is noted that only a limited number of nanoencapsulation techniques can produce particles smaller than 10 microns, and those techniques are associated with significant loss of polymer, the material to be encapsulated, or both. This is particularly problematic where the active agent is an expensive entity such as certain medical agents. The method described herein provides a means for producing nano-sized particles with minimal loss of materials. The described methods can result in product yields greater than 80% and encapsulation efficiencies as high as 100%.

V. Compositions Containing Multi-Walled Nanoparticles

The multi-walled nanoparticles prepared from the methods described in Section IV can be combined with one or more pharmaceutically acceptable excipients to form composition or formulation suitable for administration to an animal or human in need thereof.

The nanoparticles can be formulated for a variety of routes of administration and/or applications. Suitable routes of administration include enteral and parenteral. Suitable dosage forms for enteral administration include, but are not limited to, tablets, capsules, caplets, solutions, suspensions, syrups, powders, or thin films. The multi-walled nanoparticles may be formulated into an enteral dosage forms. Suitable enteral dosage forms are described above in Section II. D.

1. Parenteral Dosage Forms

Exemplary routes of parenteral administration include, but are not limited to, intrathecal, intracardiac, intraosseous (bone marrow), stereotactic-guided delivery, infusion delivery, CNS delivery, stereo-tactically administered delivery, orthopaedic delivery (for example, delivery to joints, into bone and/or bone defects) cardiovascular, inter- and intra- and para-ocular (including intravitreal and scleral and retrobulbar and sub-tenons delivery), intradermal, intramuscular, intraperitoneal, intraveneous, and subcuntaneous. Suitable dosage forms for parenteral administration include solutions and suspensions. Formulations for parenteral administration can contain one or more excipients, such as solvent, dispersing agents, pH modifying agents, buffers, preservatives, surfactants, emulsifying agents, and combinations thereof.

VI. Methods of Using Multi-Walled Nanoparticles

The multi-walled nanoparticles prepared by the methods described herein can be used to provide controlled drug delivery. In one embodiment, the nanoparticles contain a biodegradable core polymer. As the core polymer degrades, the agent is released from the core. The agent can then diffuse through the one or more walls of the multi-walled nanoparticle, and/or be release as the one or more walls degrade. For example, for double-walled nanoparticles, agent can diffuse through the shell polymer, and/or be released as the shell polymer degrades.

A combination of core and shell polymer in double-walled nanoparticles can be selected so that the agent is released over a specific time period at a specific location in the GI tract. Similarly with respect to nanoparticles containing three or more walls, a combination of the properties of the various walls that form the nanoparticles be selected so that the agent is released over a specific time period at a specific location in the GI tract.

The nanoparticles can also be used to encapsulate agents which are not designed to be released in vivo. For example, an imaging agent can be encapsulated in a multi-walled nanoparticle containing a non-degradable core polymer and a bioadhesive shell polymer. The shell polymer adheres the particles to the tissue surface while the imaging agent allows particles to be imaged using an appropriate device.

In yet another embodiment, the nanoparticles contain agents that are not designed to be administered to a patient. The polymers can be selected to provide the desired release characteristics for the particular application of the multi-walled nanoparticles.

EXAMPLES

Example 1

Synthesis and Characterization of Bioadhesive Polymers

Materials

Poly(lactic-co-glycolic acid) (Resomer RG 502, 50:50; i.v. range 0.16-0.24 dL/g in $CHCl_3$), was purchased from Boehringer-Ingelheim, Inc. (Ridgefield, Conn.), PLGA (75:25; i.v. 0.67 dL/g in $CHCl_3$) and D,L-poly(lactic acid) (D,L-PLA; i.v. 0.21 dL/g in $CHCl_3$) were purchased from Birmingham Polymers, Inc. (Pelham, Ala.); these polymers were stored at $-15°$ C. until use. Poly(methyl methacrylate) (PMMA, atactic; MW: ~25,000) was obtained from Polysciences, Inc. (Warrington, Pa.) and stored at room temperature. Poly(butadiene-co-maleic anhydride) (PBMA, 15 kDa) and poly(ethylene-co-maleic anhydride) (PEMA, 400 kDa) were purchased from Polysciences, Inc. (Warrington, Pa.), while polycaprolactone (PCL, 65 kDa) and the amino acid conjugates were obtained from Sigma-Aldrich Co. (St. Louis, Mo.). All solvents were of the highest commercial grade available.

Polymer Synthesis

All bioadhesive poly(butadiene-co-maleic anhydride) (pBMA)-derivative and poly(ethylene-co-maleic anhydride) (pEMA)-derivative polymers were synthesized via a ring-opening, side-chain conjugation reaction in dimethyl sulfoxide (DMSO). 500 mg of each polymer backbone, poly(butadiene-co-maleic anhydride) 1:1 (PBMA, 15 kDa) and poly(ethylene-co-maleic anhydride) 1:1 (PEMA, 400 kDa), was dissolved at a concentration of 1 w/v % with one of three amino acid derivatives, phenylalanine, tyrosine, or DOPA in dimethyl sulfoxide (DMSO) (Mallinckrodt, Hazelwood, Mo.).

The molar ratio of side chain to backbone was determined by assuming side chain addition to each site of attachment, the maleic anhydride residues (e.g. for reacting PBMA with DOPA, (side chain molar mass/monomer molar mass)*polymer mass=side chain mass, (197 amu/152 amu)*500 mg=650 mg). The DMSO solution was stirred and heated on a thermostat controlled stirring hot plate (Fisher Scientific, Pittsburgh, Pa.) set to $70°$ C. and 500 revolutions per minute. The flasks in which the reaction took place were sealed by rubber stoppers to minimize any atmospheric water vapor ingress, and the reaction was run for 12 hours.

At the completion of the reaction, the solution was allowed to cool to room temperature. Twice the volume of room temperature distilled water was added to dilute the DMSO prior to dialyzing. Dialysis was performed in 4 L stainless steel vessels using 1 cm of 10 kDa cut-off SnakeSkin tubing (Thermo Scientific, Rockford, Ill.) for every 3 ml of added liquid with room for increased water absorption so that the polymer remained and any un-reacted side chain as well as DMSO was dialyzed and discarded. At least 5 water changes were performed over the course of 3 days to ensure minimal residual organic solvent and un-reacted side chain. After dialysis, the remaining aqueous polymer solution was lyophilized (VirTis, Gardiner, N.Y.) yielding dry powders. Each batch produced approximately 600 mg of side chain grafted polymer with a yield of ~50-60%. The chemical structures of the polymers are shown in FIG. 1.

Nuclear Magnetic Resonance (NMR) Analysis of Bioadhesive Polymers

Both polymer backbones, PBMA and PEMA, along with their bioadhesive derivatives were dissolved in deuterated DMSO (D6-DMSO, Cambridge Isotope Laboratories, Andover, Mass.) at a concentration of 25 mg/ml. Each polymer solution was loaded into a 5 mm thin wall 300 MHz NMR sample tube (Wilmad Lab Glass, Vineland, N.J.) and an average of sixteen scans was acquired for analysis. $^1$H NMR analysis was performed on a Bruker DPX 300 MHz spectrometer equipped with a BBO probe and processed using TopSpin 1.3 software (Bruker, Billerica, Mass.). Peak assignment of PEMA-derived polymers was confirmed by multiplicity edited hetero-nuclear single quantum coherence $^1$H NMR, performed on a Bruker Ultraspin 400 MHz spectrometer (Bruker, Billerica, Mass.).

For the PBMA-derived polymers, the peaks corresponding to the olefinic protons present in the backbone ($\delta$~4.4-5.5) was used as a basis of comparison with the hydrogen atoms bound to the aromatic carbons present in the side chains ($\delta$~6-7). Since each monomeric unit of the PBMA-derived polymers should contain two olefinic backbone protons, the area under the associated peaks was assigned a value of 2 and all other peak areas were measured relative to the peak for the olefinic protons. Each of the grafted side chains contains an aromatic ring not present in PBMA or PEMA. Assuming 100% attachment to all maleic anhydride residues, the peak area associated with the hydrogens in the aromatic ring of phenylalanine would have an area ratio of 5:2, tyrosine would have an area ratio of 4:2, and DOPA would have an area ratio of 3:2, as compared to the backbone hydrogens bound to the doubly bonded carbons in PBMA or to the carbons bound to three other carbon atoms in PEMA. By comparing the measured peak area ratio to the theoretical peak area ratio, a measure of side chain attachment efficiency is provided in Table 2.

TABLE 2

Side Chain Attachment Efficiency

| Polymer | Side Chain Attachment Efficiency |
|---|---|
| PBMAP | 79% |
| PBMAT | 86% |
| PBMAD | 75% |
| PEMAP | 98% |
| PEMAT | 73% |
| PEMAD | 91% |

PBMA-derived bioadhesive polymers exhibit approximately 70-90% side chain attachment efficiency.

A similar analysis was performed for the PEMA-derived polymers; however, since PEMA does not contain any olefinic protons, the two methine protons of maleic anhydride were used were used in the analysis. PEMAP, PEMAT, and PEMAD exhibit side chain attachment efficiencies of 98%, 73%, and 91%, respectively. Differences in attachment efficiency may have resulted from differing confirmations of the polymer during side chain attachment that could promote or hinder the reaction based upon steric constraints.

Peak assignment was confirmed by multiplicity edited hetero-nuclear single quantum coherence (HSQC) $^1$H NMR. Confirmation was based on the phase of the carbon atoms, which is dependent on the number of bound hydrogens. Using HSQC, methyl and methine carbons appeared in phase and methylene carbons in opposite phases.

Polymer Probe Preparation

Each of the bioadhesive polymers tested was solvent cast onto the heads of glass-headed pins ($\Phi$=2-3 mm). To prepare 5 w/v % solutions for dip coating, acetone was the solvent for PBMA, PEMA, and their derivative polymers and ethyl acetate was used for Polycarbophil AA-1 (Noveon, Cleveland, Ohio). Glass-headed pins were dipped and dried three times to ensure a continuous polymer coating prior to bioadhesion testing.

Contact Area Determination and Validation

Contact area was calculated by measuring the diameter of each polymer probe and quantifying probe penetration depth, or compressive deformation of the intestinal tissue, during each test. Given probe radius (R) and penetration depth (a), the radius of the cross sectional area of contact (r) can be calculated, $r=(R^2-(R-a)^2)^{1/2}$, using the Pythagorean Theorem. Assuming spherical polymer probes, the circular cross-sectional contact area (A) is calculated as $A=\pi r^2=\pi(R^2-(R-a)^2)$.

To experimentally validate the cross-sectional area calculation, glass-headed pins were dry powder coated in 80-mesh carbon black (Sigma Aldrich, St Louis, Mo.) and then loaded into the TA bioadhesion testing setup. In place of tissue, double-sided foam tape (3M, St Paul, Minn.) was used so that the carbon black powder would transfer to the tape in the area contacted by the probe. The cross-sectional area of contact was calculated using the above described method and then compared to the area of carbon black left on the tape as determined by NIH ImageJ analysis of digital photographs.

The projected cross-sectional area calculated based upon the probe radius and penetration depth measured by the TA were compared against the area of the carbon black residue left on double-sided foam tape as analyzed by ImageJ. The two mean values of cross-sectional contact area were statistically insignificantly different ($p>0.05$) as analyzed by one-way analysis of variance (ANOVA) (N=6), experimentally validating the compressive deformation-based cross-sectional contact area calculation.

Tensile Bioadhesion Testing

Bioadhesive tensile fracture strength and tensile work were performed on a Texture Analyzer TA.XTPlus (TA) (Texture Technologies, Scarsdale, N.Y.). Intestinal tissue was excised from 200-300 g albino, male, Sprague-Dawley rats immediately post mortem. Tissue was sectioned into 3 cm lengths and stored in phosphate buffered saline (PBS) on ice for a maximum of 4 hours until bioadhesion testing. The tissue lumen was rinsed with 10 ml of PBS then cut along the anti-mesenteric boarder and placed mucus-side up in PBS on a water heated tissue holder set to 37° C. to mimic physiological conditions.

Bioadhesion testing began with the polymer probe approaching the intestinal mucus at 0.5 mm/s until a contact force of 5 gF was reached. Once the desired contact force was reached, the probe ceased motion and remained in place for a predetermined period of time to allow for polymer hydration and adhesive bond formation. PBMA and its derivative polymers were tested using a contact time of 7 minutes, as previously reported in our lab. PEMA and its derivatives had not sufficiently hydrated after a period of 7 minutes and so a contact time of 14 minutes was used. In order to compare the bioadhesive polymers to the commercial bioadhesive, Polycarbophil AA-1, Polycarbophil-coated probes were tested both at 7 and 14 minutes contact time. After the contact time elapsed, the probe was retracted from the mucus at 0.5 mm/s while measuring tensile load caused by bioadhesion. The peak tensile load normalized by the cross-sectional contact area yields a measure of bioadhesive fracture strength and the area under the tensile force-distance curve measures tensile work. Both fracture strength and tensile work have shown strong correlations with the in vivo performance of bioadhesive polymers. All polymers were tested six times and each intestinal tissue segment was used for a maximum of 30 minutes. Tissue explants from a total of 5 rats were used and all animal procedures were performed in accordance with NIH and IACUC guidelines.

Polyacrylic acids consist of a polyethylene backbone that has a high density of hydrophilic carboxylic acid side-groups (see FIG. 1a). Carboxylic acid residues confer strong bioadhesive properties achieved by a high degree of hydrogen bonding and promote water solubility. Once dissolved, polyacrylic acids no longer provide any substantive bioadhesive linkage between an oral dosage form and the GI mucosa. By comparison, as an anhydride polymer, PBMA is initially hydrophobic and water insoluble. As the maleic anhydride sidegroups hydrolyze to form dicarboxylic acids, the polymer increases its carboxylic acid content over time in aqueous media and therefore increases both bioadhesiveness via hydrogen bonding and as water solubility.

Through the process of adding aromatic amino acid side chains to PBMA, the maleic anhydride is converted into a carboxylic acid and creates an amide bond to the amino acid forming the side chain. In the case of phenylalanine addition (PBMAP), the carboxylic acid and the aromatic ring of the amino acid are added as a side-group presenting both hydrophilic and hydrophobic moieties. Tyrosine and DOPA addition (PBMAT and PBMAD) include a singly and doubly hydroxyl-substituted aromatic side group increasing the hydrophilicity and hydrogen bonding capacity of the polymers (see chemical structures in FIG. 1). Additionally, the physiochemical properties of the DOPA side chains on PBMAD may provide appropriate spacing and partial charge distribution for hydroxyl groups to form bonds with any multivalent cations found within the GI mucosa. Free DOPA has been shown to chelate iron in both in vitro and in vivo settings. Proteins bearing DOPA functionality, such as mussel adhesive proteins, have demonstrated strong iron binding capabilities. Without being bound by theory, it is believed that hydroxyl groups on the DOPA side chains bind ferric ions and other multivalent cations present in the GI mucosa.

Figure 2A:
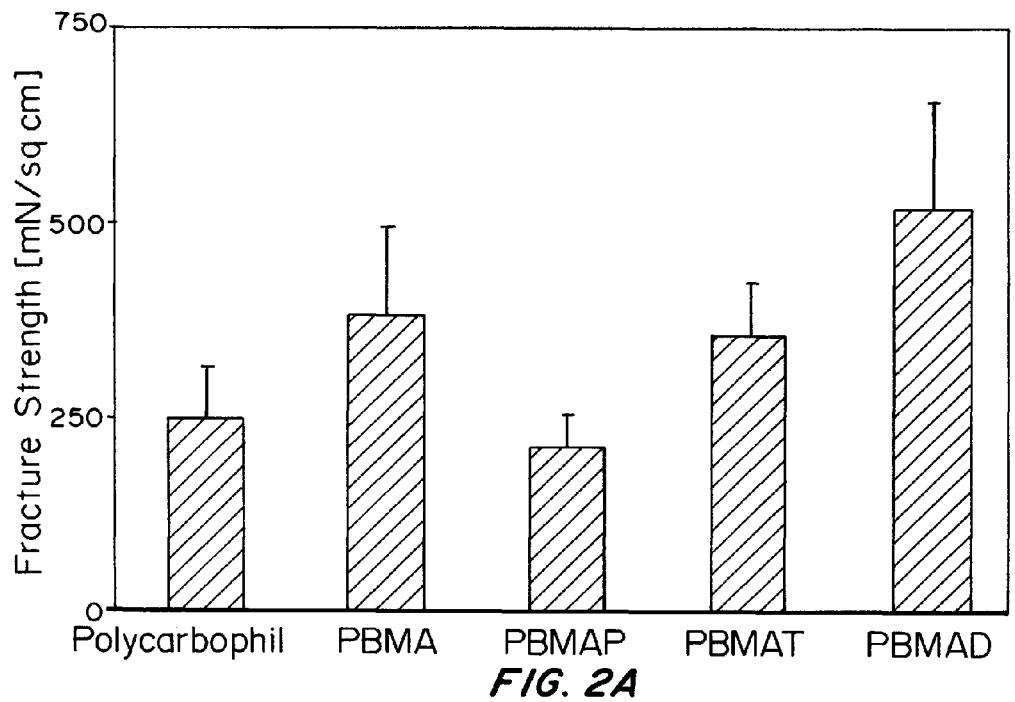
FIG. 2a is a bar graph comparing the fracture strength ($mN/cm^2$) of a polycarboxylic acid (polycarbophil) with poly (butadiene-co-maleic anhydride) (PBMA) and a series of PMBAs having bioadhesive groups grafted to the polymer backbone.

Mean fracture strength of Polycarbophil AA-1 (a commercially utilized polyacrylic acid-derived bioadhesive), PBMA, and its derivatives are plotted in FIG. 2a. The bioadhesive bond between Polycarbophil and freshly excised rat intestinal mucosal tissue exhibits $245.7 \pm 65.3$ mN/cm$^2$ peak strength prior to mucoadhesive bond failure, or fracture strength (N=6). PBMA, PBMAP, PBMAT, and PBMAD demonstrate 1.54×, 0.86×, 1.46×, and 2.12× the mean fracture strength of Polycarbophil respectively. Although there is no statistically significant difference among the fracture strengths ($p>0.05$), there is a linear trend towards increased fracture strength from phenylalanine to tyrosine to DOPA functional polymers in order of their biochemical synthetic pathway in humans.

Figure 2B:
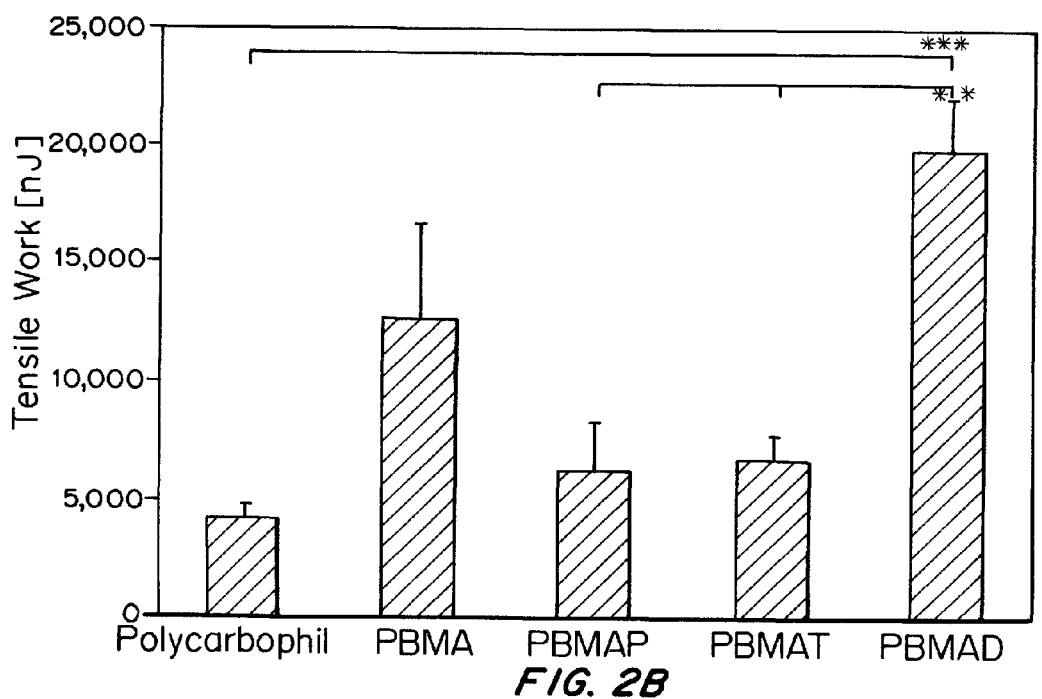
FIG. 2b is a bar graph comparing the tensile work (nJ) of a polycarboxylic acid (polycarbophil) with poly(butadiene-co-maleic anhydride) (PBMA) and a series of PBMAs having bioadhesive groups grafted to the polymer backbone. The values for facture strength and tensile work have been corrected for the surface area of contact between the intestinal tissue and the bulk polymer surface.

With respect to the area under the bioadhesive force-distance curve, or tensile work, Polycarbophil exhibits $4093 \pm 177$ nJ. PBMA, PBMAP, PBMAT, and PBMAD demonstrate 3.08×, 1.53×, 1.64×, and 4.83× the mean bioadhesive tensile work of Polycarbophil respectively (see FIG. 2b). While the linear trend of increasing bioadhesion along the biochemical synthetic pathway is not present in the tensile work comparison, the overall order of adhesiveness is preserved with the exception of Polycarbophil and PBMAP reversing order as last and next to last. PBMAD exhibits a statistically significantly higher mean bioadhesive tensile work than PBMAT and PBMAP ($p<0.01$), as well as Polycarbophil ($p<0.001$). The high tensile work and fracture strength demonstrated by PBMAD may result in part from the exceptional ability to bind multivalent cations present in mucus, in addition to standard hydrogen bonding due to carboxylic acid groups and other potential bioadhesive mechanisms.

PEMA has a polyethylene-based backbone that lends itself to a greater degree of crystallinity than the polybutadiene-rubber-based backbone of PBMA (FIG. 1). Additionally, PEMA has a significantly higher molecular weight (Mw=400 kDa) and smaller repeat unit (MR=126 Da) than PBMA (Mw=10-15 kDa, MR=151 Da). The increased molecular weight and anhydride density of PEMA as compared to PBMA are indicative of greater bioadhesive properties based on previous studies with other polymers. However, the increased crystallinity of the polyethylene backbone reduces the hydration rate and therefore bioadhesion testing performed with 7 minutes of contact time between the polymer probes and intestinal mucosa, as with the PBMA-derived polymers, demonstrated negligible bioadhesion. Doubling the contact time to 14 minutes allowed for sufficient hydration of PEMA and yielded measureable bioadhesive properties. The difference in contact time obviates direct comparison between PBMA- and PEMA-derived polymers. Therefore, the bioadhesive properties of Polycarbophil were tested with 14 minutes contact time to provide a common basis for comparison.

Figure 3A:
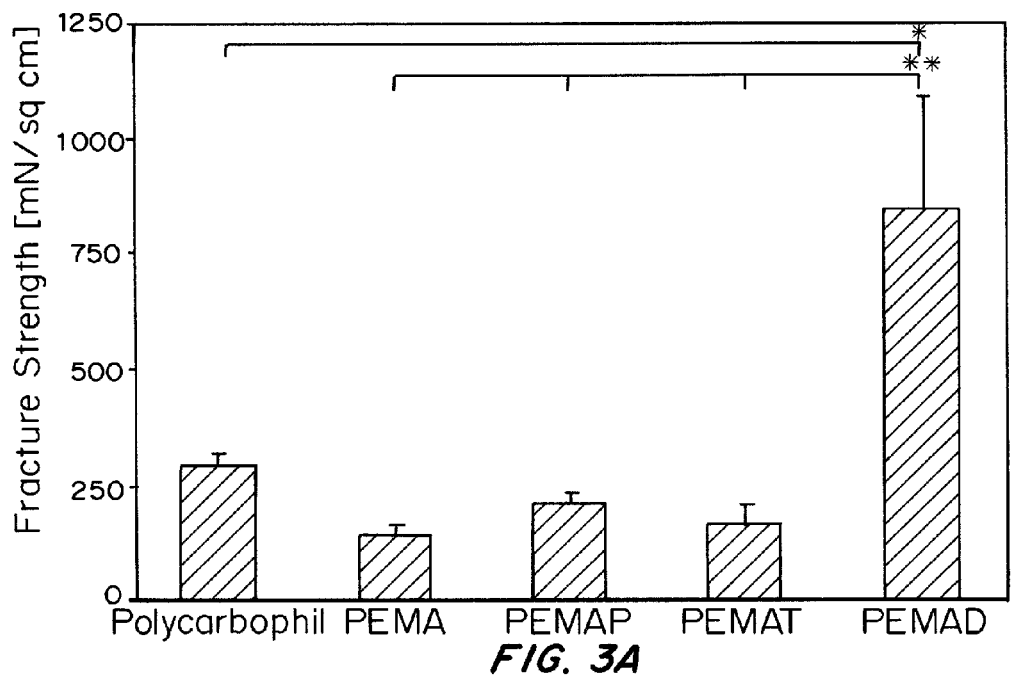
FIG. 3a is a bar graph comparing the fracture strength ($mN/cm^2$) of a polycarboxylic acid (polycarbophil) with poly (ethylene-co-maleic anhydride) (PEBA) and a series of PEBAs having bioadhesive groups grafted to the polymer backbone.

Under the 14 minutes contact time testing conditions, Polycarbophil produced a mean bioadhesive fracture strength of $334.9 \pm 33.4$ mN with freshly excised rat intestinal tissue, statistically similar to the fracture strength measured using 7 minutes hold time ($p>0.05$) (see FIG. 3a). PEMA, PEMAP, PEMAT, and PEMAD produced 0.42×, 0.61×, 0.50×, and 2.5× the mean bioadhesive fracture strength of Polycarbophil tested under the same conditions (FIG. 3a). PEMAD produced the greatest bioadhesive fracture strength of any polymer tested in this study, statistically significantly higher than each of the other polymers PEMA derivatives ($p<0.01$) and Polycarbophil ($p<0.05$) tested under the same conditions, indicating that it is a very strong bioadhesive. The linear trend of increasing bioadhesive fracture strength of PEMA-derived polymers coinciding with the biochemical synthetic pathway of DOPA is not present as with the PBMA derivatives. Instead there is a sharp increase in bioadhesiveness from PEMAP and PEMAT to PEMAD. The increase may be due in part to the ability of DOPA-functionalized bioadhesives to bind multivalent cationic species in mucus and also in part to the increased hydrophilicity afforded by the two hydroxyls present on the aromatic rings of the DOPA side chains, in addition to other bioadhesive mechanisms.

Figure 3B:
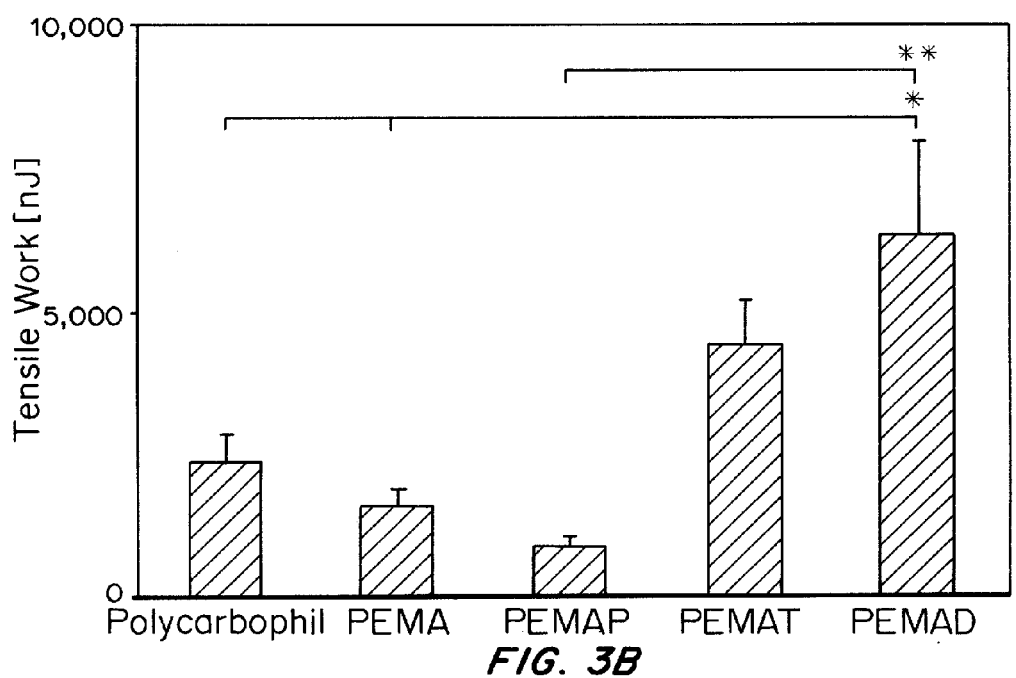
FIG. 3b is a bar graph comparing the tensile work (nJ) of a polycarboxylic acid (polycarbophil) with poly(ethylene-co-maleic anhydride) (PEBA) and a series of PEBAs having bioadhesive groups grafted to the polymer backbone. The values for facture strength and tensile work have been corrected for the surface area of contact between the intestinal tissue and the bulk polymer surface.

Mean tensile work of the PEMA-derived polymers is compared with Polycarbophil in FIG. 3b. After 14 minutes of contact time, Polycarbophil produces significantly less tensile work of bioadhesion than after 7 minutes with a mean of $2,299 \pm 575$ nJ. The statistically significant, 44% reduction in mean tensile work ($p<0.05$) of Polycarbophil tested with 14 minutes hold time as compared to 7 minutes may be due to the increased hydration of the polymer leading to decreased mechanical. PEMA, PEMAP, PEMAT, and PEMAD produce 0.67×, 0.37×, 1.9×, and 2.8× the mean tensile work of Polycarbophil respectively. PEMAD produced a statistically significantly higher mean bioadhesive tensile work than Polycarbophil ($p<0.05$), PEMA ($p<0.05$), and PEMAP ($p<0.01$). In both PBMA- and PEMA-derivative polymer testing the DOPA functionalized polymer produced the highest mean bioadhesive fracture strength and tensile work.

Having different contact times due to different hydration rates complicates direct comparison between the PEMA- and PBMA-derived bioadhesives. Yet, the strongest adhesion was observed in DOPA-functionalized polymers in all tested conditions. In particular the increase in mean bioadhesive fracture strength of PEMAD compared to the other PEMA-derived polymers and Polycarbophil ($p<0.01$) strongly implicates the catechol functionality in promoting bioadhesion. The catechol functional groups may play a role in multivalent cationic binding as they do in other species.

At a hold time of seven minutes, all of the polymers except PBMAP exceeded the mean maximum recorded manometric pressure of 213 mN/cm$^2$ in rat small intestines. While at a hold time of 14 minutes, only Polycarbophil and PEMAD exceeded 213 mN/cm$^2$. Of all the polymers tested, only PBMAD and PEMAD exceed the 440 mN/cm$^2$ manometric pressures recorded in the human proximal small intestines during phase 3 of digestion. While manometric pressure is not a direct measure of the force exerted by the GI on an oral dosage form, it provides a guideline for predicting success of bioadhesive dosage forms. Mucus turnover and cohesive failure strength of the mucus lining also play significant roles in the in vivo performance of bioadhesives. In light of the fracture strength data presented in FIGS. 2a and 3a, the DOPA-derived polymers show promise for use as bioadhesives in oral drug delivery.

Figure 9:
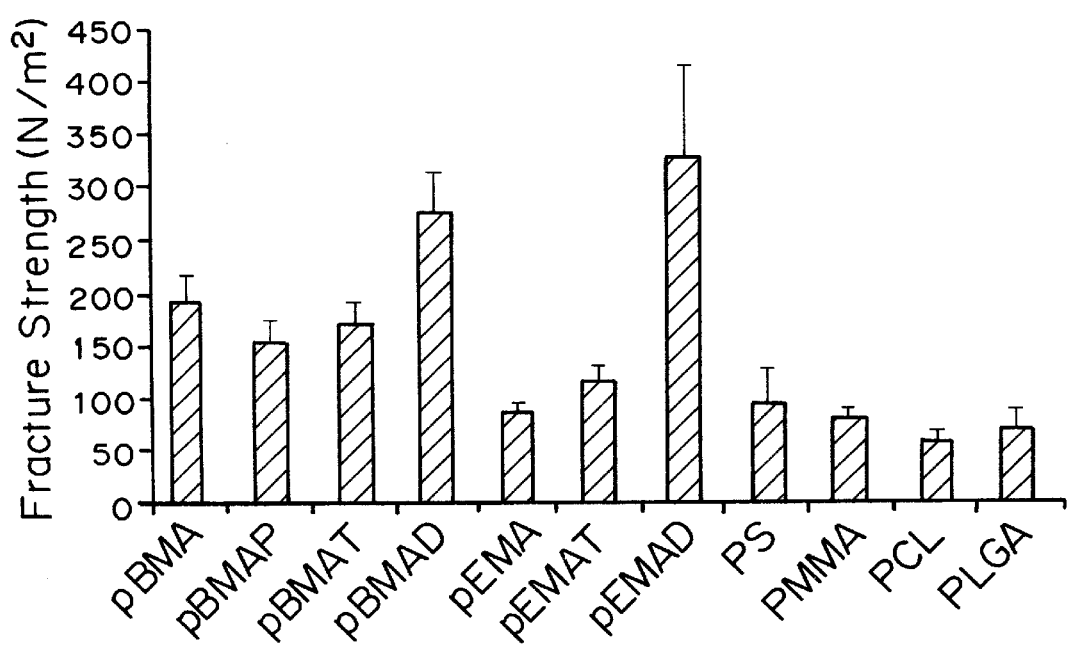
FIG. 9 is a bar graph plotting the plotting the adhesive forces of bulk polymers to freshly excised rat intestinal tissue. Bioadhesion was measured in terms of fracture strength (mN/cm$^2$) as described in Example 1 for samples of poly(butadiene maleic anhydride) (pBMA), poly(butadiene maleic anhydride-co-phenylalanine) (pBMAP), poly(butadiene maleic anhydride-co-tyrosine) (pBMAT), and poly(butadiene maleic anhydride-co-L-dopamine) (pBMAD), poly(ethylene-co-maleic anhydride) (pEMA), poly(ethylene maleic anhydride-co-phenylalanine) (pEMAP), poly(ethylene maleic anhydride-co-tyrosine) (pEMAT), poly(ethylene maleic anhydride-co-L-dopamine) (pEMAD); posystyrene (PS), polymethyl methacrylate (PMMA), polycaprolactone (PCL), and poly(lactic-co-glycolic)acid (PLGA).

Using a similar method, the fracture strength of a number of polymers described in Examples 1 and 3 was determined. Each polymer was cast on to the heads of glass-headed pins ($\Phi$=2-3 mm). The glass-headed pins were dipped three times into a 5 w/v % solution of polymer in dichloromethane and dried to ensure continuous polymer coating prior to fracture strength determination. Each polymers was tested six times (n=6) as described above using rat intestinal tissue segments. The results are shown in FIG. 9.

Fracture strength was determined by normalizing the peak tensile load (found at the beginning of the fracture) to the projected cross-sectional area (PCSA). PCSA=$\pi(r^2-[r-a]^2)$ where r is the radius of the sphere as measured by calipers and a is the depth of penetration. Tensile work was calculated as the area under the tensile load versus distance curve.

Cloud Point Determination

The cloud point of a polymer solution corresponds to the transition from a translucent to a metastable cloudy turbid state due to the separation of the solution into two distinct phases, one with a high relative polymer concentration and another with a low relative polymer concentration.

For the each formulation, THF was selected as the solvent for the core polymer and ethanol was selected as the solvent for the shell polymer; other polymer/solvent combinations have also been successfully evaluated for use with sPIN. To determine the cloud point of the each core polymer solution, ethanol was added in 100 μL increments to a 2% w/v polymer solution until the solution became turbid and resulted in no increase in the turbidity of the solution with further the further addition of ethanol without precipitation of the polymer. Once the cloud point was determined, the cloud point testing was repeated using a 2% w/v solution of the shell polymer in ethanol to ensure the presence of the second polymer did not affect the cloud point.

To prepare multi-walled particles with different core-polymers, the cloud points of PMMA, PLGA (75:25), PLGA (50:50) and D,L-PLA in THF with pBMAD in ethanol were evaluated. In addition, the cloud point of PMMA in THF with pBMAP, pBMAT, pBMAD, pEMAP, pEMAT and pEMAD in ethanol was determined in order to prepare particles with different shell-polymers.

As shown in Table 3, the cloud point of each core polymer solution was successfully induced with the addition of a sufficient volume of ethanol, between 1.280 and 2.801 mL of ethanol per mL of THF. This difference in the required volume of ethanol to induce cloud point formation is likely the result of the solubility parameter of each polymer in THF.

Additionally, to confirm that the presence of the secondary shell polymer does not affect the cloud point of the core polymer, these tests were performed using 2% solutions of the shell polymer in ethanol. The results showed that the presence of the bioadhesive shell polymer in the system did not affect the cloud point of the core polymer, suggesting that the phase separation in this system is the result of a polymer/solvent/non-solvent system rather than polymer/polymer interactions previously used in the preparation of double-walled microspheres.

TABLE 3

Cloud Point Determination Results for PMMA, PLGA (75:25), PLGA (50:50) and D,L-PLA in THF

| Polymer | Solvent 1 (S1) | Solvent 2 (S2) | Cloud Point ($mL_{S2}/mL_{S1}$) |
|---|---|---|---|
| PMMA | THF | Ethanol | 2.801 |
| PLGA (50:50) | THF | Ethanol | 1.560 |
| PLGA (75:25) | THF | Ethanol | 2.519 |
| D,L-PLA | THF | Ethanol | 1.280 |

Example 2

Fabrication of Double-Walled Nanospheres Using Sequential Phase Inversion Nanoencapsulation (sPIN)

Fabrication of Double-Walled Nanospheres with PMMA-Cores and Varied Shell Polymers To fabricate double-walled nanospheres consisting of PMMA-cores with various shell polymers, the appropriate volume of 2% w/v solution of each shell polymer in ethanol was added to a 2% w/v solution of PMMA in tetrahydrofuran (THF) until the cloud point for PMMA was reached. This solution was then rapidly added to a non-solvent bath (petroleum ether) with a solvent to non-solvent ratio of 1:75 and stirred for two minutes to cure the nanospheres. The resulting nanospheres were filtered using a 0.2 micron PTFE filter in a positive pressure filtration column (Millipore, Inc.; Billerica, Mass.) and lyophilized for 24 hours.

Fabrication of Double-Walled Nanospheres with pBMAD Shells and Varied Core Polymers To prepare nanospheres consisting of a pBMAD-shell with various core polymers, the appropriate volume of 2% w/v solution of pBMAD in ethanol was added to a 2% w/v solution of each core polymer in THF until the cloud point for the core polymer was reached. This solution was then rapidly added to a non-solvent bath (petroleum ether) with a solvent to non-solvent ratio of 1:75 and stirred for two minutes to cure the nanospheres. The resulting nanospheres were filtered using a 0.2 micron PTFE filter in a positive pressure filtration column (Millipore, Inc.; Billerica, Mass.) and lyophilized for 24 hours.

Characterization of Double-Walled Particles

The nanospheres were characterized using a Beckman Coulter LS 230 Laser Diffraction Particle Size Analyzer, as Perkin Elmer Spectrum One FTIR, and a Perkin Elmer DSC7 calorimeter. Scanning Electron Microscopy (SEM) was performed using a Hitachi 2700 SEM equipped with a lanthanum hexaboride gun and a Philips 410 TEM.

Figure 4:
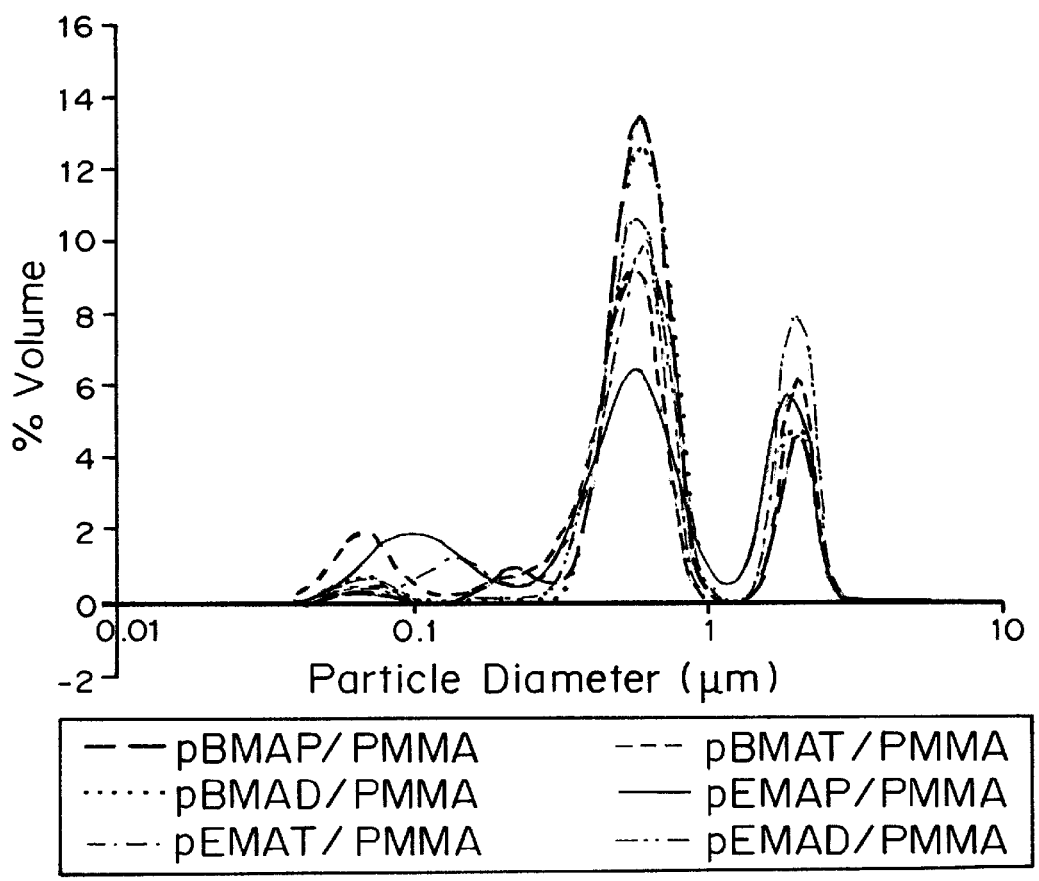
FIG. 4 is a plot showing the particle size distributions measured for double-walled nanoparticles formed from a polymethyl methacrylate core polymer and a poly(butadiene maleic anhydride-co-phenylalanine) shell (pBMAP/PMMA, solid black line), a poly(butadiene maleic anhydride-co-tyrosine) shell (pBMAT/PMMA, dashed black line), a poly (butadiene maleic anhydride-co-L-dopamine) shell (pBMAD/PMMA, dotted black line), a poly(ethylene maleic anhydride-co-phenylalanine) shell (pEMAP/PMMA, solid grey line), a poly(ethylene maleic anhydride-co-tyrosine) shell (pEMAT/PMMA, dashed grey line), and a poly(ethylene maleic anhydride-co-L-dopamine) shell (pEMAD/PMMA, dotted grey line).

Laser diffraction particle size analysis revealed that nanospheres the sPIN process using 2% w/v polymer solutions results in a biphasic distribution of particle sizes, with one population of particles in the range of 500-600 nm and the second population in the range of 1.5-2.5 microns. The particle size distribution for particles prepared using a PMMA core polymer and various shell polymers is shown in FIG. 4.

The production of particles in the 500-600 nm range is consistent with the preparation of single-walled nanoparticles using the PIN method. In PIN, particle size is directly related to the polymer solution viscosity, a function of polymer concentration. Like PIN, this method requires the use of dilute polymer solutions to produce discreet spheres, typically less than 5% w/v, with higher concentrations resulting in the formation of polymeric membranes and networks. The secondary population of particles in the 2 µm range most likely indicates the presence of aggregates.

To evaluate the morphology and aggregation of the particles, scanning electron microscopy was used to visualize the nanospheres. SEM confirmed that the majority of the nanospheres possessed a diameter of about 500 nm. In contrast to the results from laser particle size analysis, the spheres appear to be fairly monodisperse. SEM revealed the presence of nanosphere aggregates, likely the result of to the bioadhesiveness of shell polymers, the processing of the spheres in hydrophobic conditions, and the effect of lyophilization as the final step in preparation. In view of these results, the larger peak detected by laser diffraction particle size analysis most likely reflects the aggregation of the 500 nm particles.

To confirm the presence of both polymers in the spheres, the nanospheres were examined using Fourier transform infrared spectroscopy (FTIR). FTIR analysis of the bulk pBMAD and PLGA as well as the double-walled formulation revealed the presence of both polymers within the nanospheres. The FTIR spectra of the double-walled formulation contains peaks that are characteristic of both the core and shell polymers, such as the ester bond of PLGA (1750 cm$^{-1}$) and the anhydride bond of pBMAD (1700 cm$^{-1}$) in the case of pBMAD/PLGA double-walled nanospheres.

Thermal analysis of the bulk polymers and double-walled nanospheres was performed using differential scanning calorimetry (DSC) to probe the interactions between to the polymers within the nanoparticles. The results of the thermal analysis are shown in Tables 4 and 5. DSC analysis of the thermal properties of the bulk polymers revealed a $T_g$ for PLGA at 42.7° C. and a $T_g$ for pBMAD at 174° C. In contrast, the pBMAD/PLGA nanospheres revlealed two glass transitions at 49.4° C. and 159.2° C., corresponding to the glass transition temperatures for the PLGA (50:50) and pBMAD, respectively. The detection of two distinct glass transition temperatures reflects a phase separation between the two polymers, consistent with the formation of double-walled nanospheres. The shift in the glass transitions of each polymer may indicate incomplete phase separation of the two polymers at the interface of the polymers within the nanospheres.

TABLE 4

Thermal analysis of double-walled nanosphere formulations prepared by sPIN with different shell polymers and PMMA cores.

| FORMULATION | | DSC | |
|---|---|---|---|
| Shell | Core | $T_{g1}$ (° C.) | $T_{g2}$ (° C.) |
| pBMAP | PMMA | 56.82 | 148.58 |
| pBMAT | PMMA | 53.44 | 161.97 |
| pBMAD | PMMA | 54.30 | 159.99 |
| pEMAP | PMMA | 59.91 | 167.51 |

TABLE 4-continued

Thermal analysis of double-walled nanosphere formulations prepared by sPIN with different shell polymers and PMMA cores.

| FORMULATION | | DSC | |
|---|---|---|---|
| Shell | Core | $T_{g1}$ (° C.) | $T_{g2}$ (° C.) |
| pEMAT | PMMA | 56.27 | 179.46 |
| pEMAD | PMMA | 55.23 | 174.96 |

TABLE 5

Thermal analysis of double-walled nanosphere formulations prepared by sPIN with pBMAD-shells and different core polymers.

| FORMULATION | | DSC | |
|---|---|---|---|
| Shell | Core | $T_{g1}$ (° C.) | $T_{g2}$ (° C.) |
| pBMAD | PMMA | 54.30 | 159.99 |
| pBMAD | PLGA (50:50) | 42.27 | 132.59 |
| pBMAD | PLGA (75:25) | 49.39 | 159.21 |
| pBMAD | D,L-PLA | 46.15 | 147.69 |

Example 3

Synthesis and Characterization of PS, PMMA, and PMMA-BMAD Nanoparticles

Materials

Polystyrene (PS) beads (500 nm) were purchased from Polysciences, Inc. (Warrington, Pa.) and stored at 4° C. until use. Suspensions were used as supplied in concentrations of 25 mg/ml. Polymethyl methacrylate (PMMA, MW=100 kDa) and polyvinyl alcohol (MW=25 kDA, 88% hydrolyzed) were purchased from Polysciences, Inc. (Warrington, Pa.) and stored at room temperature. Poly(butadiene maleic anhydride-co-L-dopamine) (PBMAD or BMAD), was provided by Spherics, Inc. (Mansfield, Mass.), and stored at room temperature. All solvents were of the highest commercial grade available.

Synthesis of PMMA Nanospheres

Solvent evaporation was used to fabricate monodisperse PMMA nanospheres. PMMA (100 kDa) was dissolved in chloroform at a concentration of 3.3% w/v to comprise the organic phase. An aqueous phase of 1% w/v polyvinyl alcohol (25 kDa, 88% hydrolyzed) was prepared and mixed under a VirTis Cyclone IQ$^2$ SENTRY microprocessor at 25,000 rpm with a straight open blade and VirTis baffled homogenizer flask. The organic phase with polymer was then added to the aqueous phase forming an o/w emulsion and continually mixed for 15 minutes. The emulsion was then added to a 1% w/v polyvinyl alcohol (25 kDa, 88% hydrolyzed) bath and mixed under an over-head stirrer for 12 hours at 3000 rpm to allow further evaporation and curing. This suspension was then centrifuged at 4000 rpm for 20 minutes and the supernatant poured off. The pellet was resuspended and washed in deionized water three times. Finally, the formulation was lyophilized for 48 hours and stored at room temperature until use.

Synthesis of PMMA-BMAD Nanospheres

Double-walled PMMA-BMAD nanoparticles were prepared using the sPIN method described above. First, PMMA (100 kDa) was dissolved in 5 ml of tetrahydrofuran (2% w/v) and, in a separate vial, BMAD was dissolved in 10 ml of ethanol (2% w/v). The polymer solutions were mixed and then rapidly added to a non-solvent bath of petroleum ether spontaneously forming nanospheres. Nanospheres were collected by positive-pressure filtration through PTFE filter paper with a pore diameter of 0.2 µm and lyophilized for 48 hours. Formulations were stored under vacuum-seal at room temperature until use.

Nanoparticle Characterization and Size Analysis

PMMA and PMMA-BMAD nanoparticles were reconstituted from powder form into an aqueous solution using 1% w/v sodium lauryl sulfate (SLS)/1% w/v polyvinylpyrrolidone (PVP) reconstitution media and bath sonication in 0.5-2% w/v suspensions. Polystyrene nanosphere suspensions were diluted with deionized water to ~1% w/v solutions from the original supplied suspensions. A Beckman Coulter LS230 Laser Diffraction Particle Size Analyzer was used to evaluate both the particle size and the particle size distribution of the nanoparticle populations.

Figure 5:
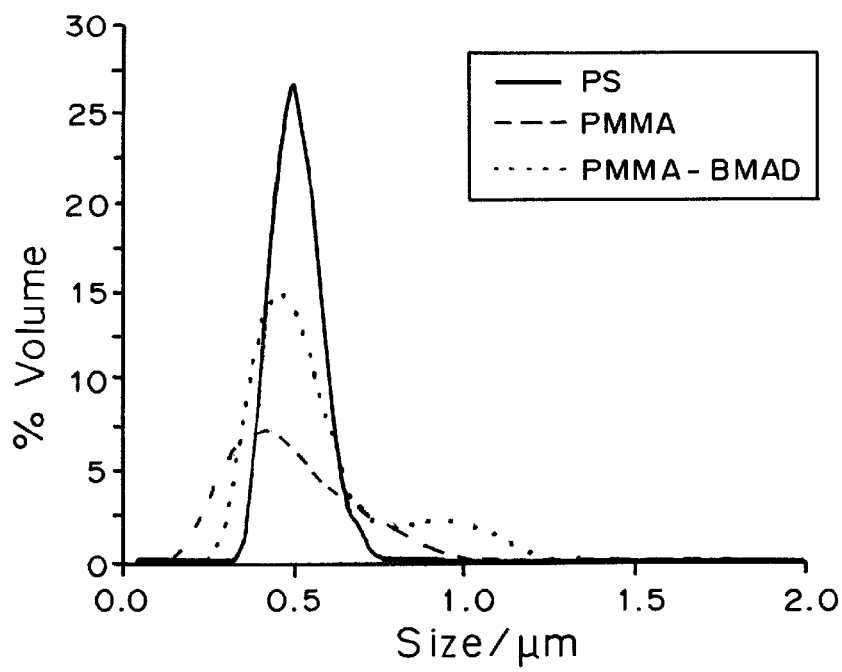
FIG. 5 is a plot showing the particle size distribution of the polystyrene (PS, solid line), polymethyl methacrylate (PMMA, dashed line), polymethyl methacrylate-poly(butadiene maleic anhydride-co-L-dopamine) (PBMAD or BMAD, dotted line) nanoparticles prepared as described in Example 3.

The average particle size of the PMMA and PMMA-BMAD nanospheres, as measured by laser diffraction, was determined to be 490±550 and 540±650 nm, respectively. The average particle size of the PS nanospheres, as purchased from Polysciences, Inc., was 540±80 nm. The particles size distribution profiles of the PS, PMMA and PMMA-BMAD nanospheres are shown in FIG. 5.

All formulations were imaged by SEM and light microscopy to evaluate morphology and aggregation. Formulations were suspended in 1% w/v HPMC and 1% w/v pluronic F127 reconstitution media at a concentration of 0.5% w/v. Drops of the suspension were placed on a slide and sealed under a cover slip with fast-drying nail polish. Slides were then imaged on a Zeiss Axiovert 200M microscope. To obtain bright field images a 40× water objective was used along with DIC and phase contrast techniques. Images were taken with a Zeiss AxioCam MRc5 digital color CCD camera.

SEM imaging confirmed that the PMMA and PMMA-BMAD nanoparticles were spherical in shape and possessed smooth external surface morphologies. Light microscopy revealed a well-dispersed population of colorless and transparent PMMA nanospheres. The PMMA-BMAD nanospheres had a tendency to aggregate into irregular clumps when in solution, and were yellow-brown in appearance due to optical properties of BMAD. When PMMA-BMAD nanoparticles were imaged under high magnification, the yellow-brown colored BMAD was observed to have coated the clear PMMA core.

To determine the weight percent of PMMA in the PMMA-BMAD nanoparticles, an extraction and chromatography detection method was used. First, a known amount (25-50 mg) of the PMMA-BMAD formulation was weighed into a vial and 5 ml of chloroform was added. The solution was mixed on an end-over-end mixer for 1 hour to ensure complete dissolution of PMMA. Then, a 1 ml sample of the solution was filtered through a 0.2 µm PTFE syringe filter into a sample vial for gel permeation chromatography. The sample elution time was detected on a Shimadzu RID-10A refractive index detector after flow (1 ml/min) through a column bank consisting of Waters Styragel HR4E and HR5E columns. The area under the distinctive PMMA peak on the refractive index versus elution time graph was calculated using Shimadzu software and compared to a linear standard curve of PMMA to directly yield the quantity of PMMA in the PMMA-BMAD formulation. 28.9% by weight of each PMMA-BMAD nanoparticle was determined to be PMMA, based upon linear regression of PMMA loading in in the spheres as determined by GPC.

Bioadhesive Measurements

Bioadhesive measurements were performed on both the bulk polymer materials as well as PS, PMMA, and PMMA-BMAD nanospheres. In all cases described herein, tissue and mucin obtained from rats was used for bioadhesion assays. Given the similarities in the anatomy and composition of the mucous in mammalian gastrointestinal systems, the assays described below can be performed using tissues and mucin from other species, for example porcine tissue and mucin.

Quantification of Bioadhesion Using Fracture Strength

The bioadhesion of bulk polymeric materials to ex vivo rat jejunum was measured with a TA.XTplus Texture Analyzer (Texture Technologies Corp., Scarsdale, N.Y.) equipped with a 1 kg load cell with 0.2 g sensitivity. All polymers were tested six times and each intestinal tissue segment was used for a maximum of 30 minutes. Nylon, hemispherical probes were coated with sample polymers by repeated cycles of dipping into molten polymer, removal, and cooling of the hemisphere. Individual probes were then fitted onto the texture analyzer load arm and a biological sample chamber placed on the stage contained freshly excised rat jejunum submerged in phosphate buffer saline, pH 7.2, with 2% w/v glucose (PBSG) with luminal side facing upward. The load arm descended at 0.5 mm/sec until a specified target force (5 g) between the sample probe and intestinal tissue was reached. This position was then held for 420 seconds followed by a rising of the load arm at 0.5 mm/sec.

Fracture strength was determined by normalizing the peak tensile load (found at the beginning of the fracture) to the projected cross-sectional area (PCSA). $PCSA=\pi(r^2-[r-a]^2)$ where r is the radius of the sphere as measured by calipers and a is the depth of penetration. Tensile work was calculated as the area under the tensile load versus distance curve.

Figure 6:
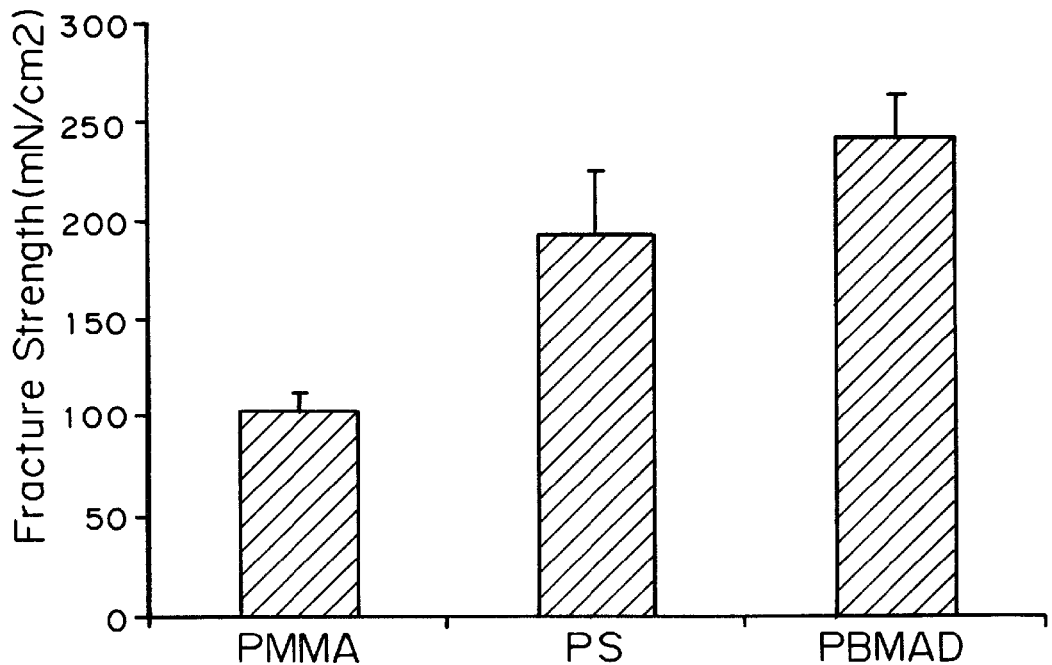
FIG. 6 is a bar graph plotting the adhesive forces of bulk materials to freshly excised rat intestinal tissue. Bioadhesion was measured in terms of fracture strength ($mN/cm^2$) using the assay described in Example 3 for samples of polystyrene (PS), polymethyl methacrylate (PMMA), poly(butadiene maleic anhydride-co-L-dopamine) (BMAD).

Bioadhesion measurements of the bulk polymeric materials were conducted for PMMA, PS, and BMAD, quantifying both in terms of fracture strength (103.6±8.3, 193.1±31.4 and 242.6±21.2 mN/cm$^2$, respectively) and tensile work (0.327±0.09 309.3±28.6 and 20445.0±5733.5 nJ, respectively). FIG. 6 depicts the bioadhesion measurements for PMMA, PS, and BMAD in terms of fracture strength.

Quantification of Bioadhesion Using the Everted Sac Method

Utilizing an everted sac assay modified from Santos, et al. *J. Control Release.* 61:113-122 (1999), the relative bioadhesion for each nanosphere formulation was determined. Male, Sprague-Dawley rats weighing 200-250 g were anesthetized with 3% isoflurane prior to a midline abdominal incision. The jejunum was removed, flushed with PBSG, and immediately immersed in fresh PBSG. Segments of jejunum, 6 cm in length, were everted, using a stainless steel rod, and ligated at both ends with silk 0-0 monofilliment sutures. The everted sac was then filled with ~2 ml PBSG and immersed in a nanosphere suspension prepared as follows. Pre-warmed (37° C.) PBSG was added to 60 mg of formulation (0.4% w/v) and bath sonicated for 5 minutes. Once the isolated loop was added to the nanosphere suspensions, samples were placed on an end-over-end mixer at 37° C. for a 30-minute period. During this incubation period nanospheres are allowed to adhere spontaneously to the everted intestinal loop. Following incubation, the everted sac is removed, placed in fresh PBS and homogenized with a Cole-Palmer Ultrasonic Homogenizer CV26 with a high gain Q horn and extender set at 40% amplitude for 30 seconds. Homogenized samples are then lyophilized for 48 hours and stored at −18° C. until analysis. The remaining nanosphere suspension is centrifuged at 4000 rpm for 5 minutes and remaining supernatant discarded. The formulation pellet is then resuspended in deionized water and centrifuged a final time at 4000 rpm for 5 minutes. Again, the supernatant is discarded. The resulting pellet is lyophilized for 48 hours and stored at −18° C. until analysis. All experiments were completed within 2 hours after jejunum harvesting (n=6).

To quantify the amount of marker polymer (polystyrene or PMMA) in both the bound (everted sac tissue sample) and unbound (remaining nanosphere suspension) samples, gel permeation chromatography was used. Tissue samples were physically cut into small pieces, added to ~5 ml PBS and homogenized on a Cole-Palmer Ultrasonic Homogenizer CV26 with a high gain Q horn and extender set at 40% amplitude for 30 seconds. Homogenized samples were then lyophilized for 48 hours resulting in a powdered tissue digest. An extraction of the marker polymer was then performed by the addition of chloroform and mixing on an end-over-end mixer for 96 hours. Extractions were then filtered through PTFE filters of 0.2 µm pore diameter to remove non-soluble debris. Filtered extractions were lyophilized for 24 hours and stored at −18° C. until analysis.

Figure 7:
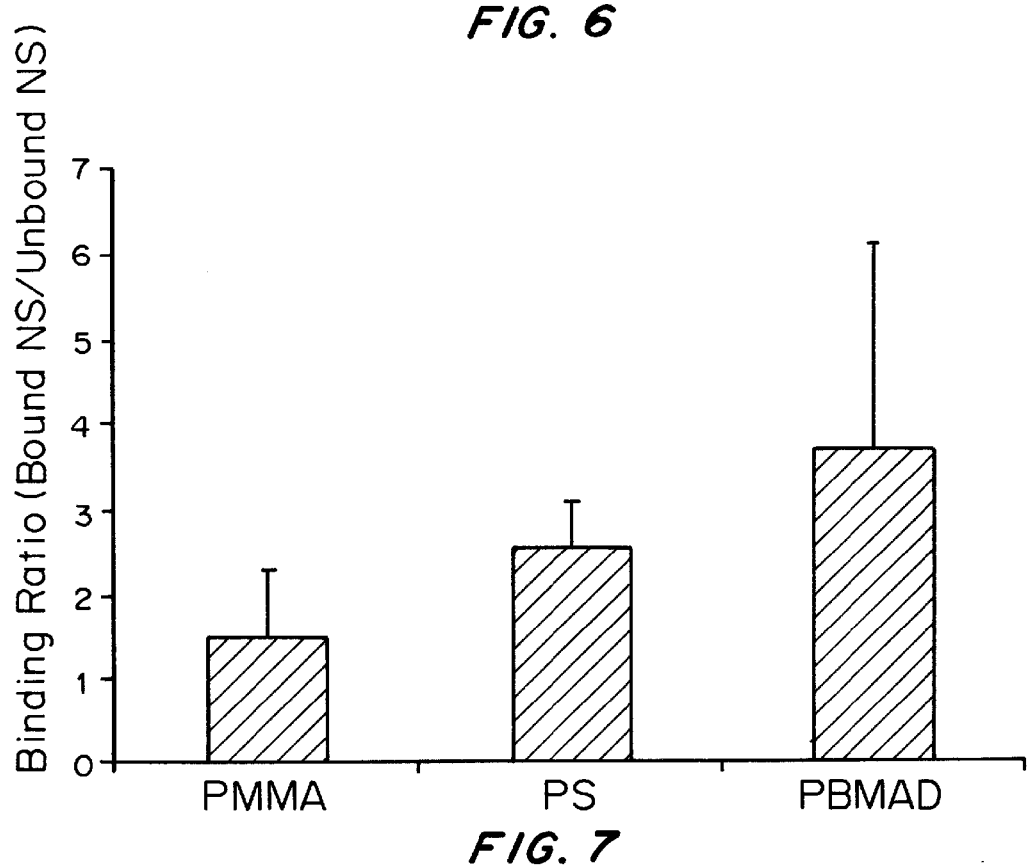
FIG. 7 is a bar graph plotting the in situ bioadhesion of PS, PMMA, and PMMA-BMAD nanospheres to everted sacs of fresh rat jejunum sections. Binding ratios of PMMA, PS and PMMA-BMAD nanosphere formulations are shown (n=10).

Lyophilized extractions were reconstituted in 1 ml of chloroform by mixing on an end-over-end mixer for 1 hour. The solution was filtered a final time through a 0.1 µm PTFE syringe filter and ran on a Shimadzu GPC equipped with Waters Styragel HR5E and HR4E columns and a Shimadzu RID-10A refractive index detector. A specific peak for the marker polymer was identified and the area under the curve calculated and related to the polymer concentration by comparison to a linear standard curve for PS and PMMA with $R^2$ values of 0.9993 and 0.9998, respectively. Since the sample volume is known, the exact amount of polymer can be calculated from the detected concentrations. Results are shown as a binding ratio (amount adhered to tissue:amount remaining is suspension) in FIG. 7 for PS, PMMA and PMMA-BMAD nanospheres. PMMA nanospheres had the lowest bioadhesion with a binding ratio of 1.49±0.82, followed by PS nanospheres with a binding ratio of 2.51±0.40 and PMMA-BMAD nanospheres had the highest bioadhesion with a binding ratio of 3.67±2.38. There was roughly a 2.5-fold increase in bioadhesion of the PMMA-BMAD nanospheres over the PMMA nanospheres with PS having an intermediate level of bioadhesion. The percent of nanoparticles bound for each sample was calculated by multiplying the ratio of the amount detected on the everted sac tissue to the total dose by 100.

Quantification of Bioadhesion by Contact Angle Measurment

Contact angles of the bulk polymer materials were measured using the procedure described by Mathiowitz, et al., Chapter 17 "Bioadhesive, Bioerodible Polymers for Increased Intestinal Uptake", pages 459-475, in *Bioadhesive Drug Delivery Systems: Fundamentals, Novel Approaches, and Development*, Marcel Dekker, Inc., New York, N.Y. (1999), which is incorporated herein by reference. Polymer films were prepared by casting 5 wt % polymer solutions in methylene chloride onto a flat surface and allowing them to dry. 5 µL drops of distilled water and rat mucin (Pel-Freez Biologicals, Rogers, Ark.) were placed on the film surface. The contact angle of both water and rat mucin with the polymer film was measured using a goniometer.

Example 4

Quantification of the Total Intestinal Uptake of PS, PMMA, and PMMA-BMAD Nanoparticles Using an In Vivo Isolated Loop Assay As discussed above, PMMA, PS, and PMMA-BMAD nanoparticles were evaluated to determine the tensile bioadhesiveness of the bulk polymer, bioadhesion of the nanospheres to everted intestinal sacs, and contact angle of the bulk polymer with rat mucin. Commercially available PS nanospheres were shown to be moderately bioadhesive, PMMA nanospheres were shown to be non-bioadhesive, and PMMA-BMAD nanospheres were shown to be highly bioadhesive.

The total intestinal uptake of non-bioadhesive PMMA nano-spheres, moderately bioadhesive PS nanospheres, and highly bioadhesive PMMS-BMAD nanospheres was quantified using and in vivo isolated loop assay. Suspensions of the nanoparticles prepared and characterized in Example 3 were utilized for in vivo experiments. Polystyrene nanospheres are supplied as a 2.5% w/v suspension and were used as received. For PMMA and PMMA-BMAD formulations the powder formulation was added to 1% w/v hydroxypropyl methylcellulose/1% w/v pluronic F127 to a final concentration of 2.5% w/v. To adequately disperse the formulations, solutions were bath sonicated for 10 minutes immediately before administration. A dosage volume of 1 ml was used in all studies and resulted in a total dose of 25 mg.

Suspensions of each nanosphere were directly administered to a specific gastro-intestinal region using an isolated loop technique. Male, Sprague-Dawley rats, weighing 200-250 g were allowed access to standard chow and water ad libitum. Rats were anesthetized with 3% isoflurane inhalation. A 6 cm length of jejunum was isolated by suture ligation with monofilament silk 0-0 sutures at each end taking care not to disrupt blood flow from mesenteric arteries. Suspensions of the nanospheres were then injected directly into the isolated region's lumen. The isolated loop was returned to the abdomen, which was then closed to maintain body temperature and moisture. Following a specified incubation period, the following samples were collect in order: 1 ml blood from portal vein, 1 ml blood from celiac artery, lungs, heart, spleen, kidneys, liver, isolated loop, rinse of isolated loop, and brain. All tissues were stored at −18° C. until further processing. Studies were ran in animal cohort groups of n=4 for each study.

The tissue samples were processed and quantitatively analyzed for polymer content by gel permeation chromatography. Tissue samples were physically cut into small pieces, added to ~5 ml PBS and homogenized on a Cole-Palmer Ultrasonic Homogenizer CV26 with a high gain Q horn and extender set at 40% amplitude for 30 seconds. Homogenized samples were then lyophilized for 48 hours resulting in a powdered tissue digest. An extraction of the marker polymer was then performed by the addition of chloroform and mixing on an end-over-end mixer for 96 hours. Extractions were then filtered through PTFE filters of 0.2 µm pore diameter to remove non-soluble debris. Filtered extractions were lyophilized for 24 hours and stored at −18° C. until analysis.

Lyophilized extractions were reconstituted in 1 ml of chloroform by mixing on an end-over-end mixer for 1 hour. The solution was filtered a final time through a 0.1 µm PTFE syringe filter and ran on a Shimadzu GPC equipped with Waters Styragel HR5E and HR4E columns and a Shimadzu RID-10A refractive index detector. A specific peak for the marker polymer was identified and the area under the curve calculated and related to the polymer concentration by comparison to a linear standard curve for PS and PMMA with $R^2$ values of 0.9993 and 0.9998, respectively. Since the sample volume is known, the exact amount of polymer can be calculated from the detected concentrations. Total intestinal uptake (as a percent) was calculated by taking the sum of all amounts detected in tissues (excluding isolated loop and loop rinse samples) divided by the total dose administered and multiplied by 100.

Figure 8:
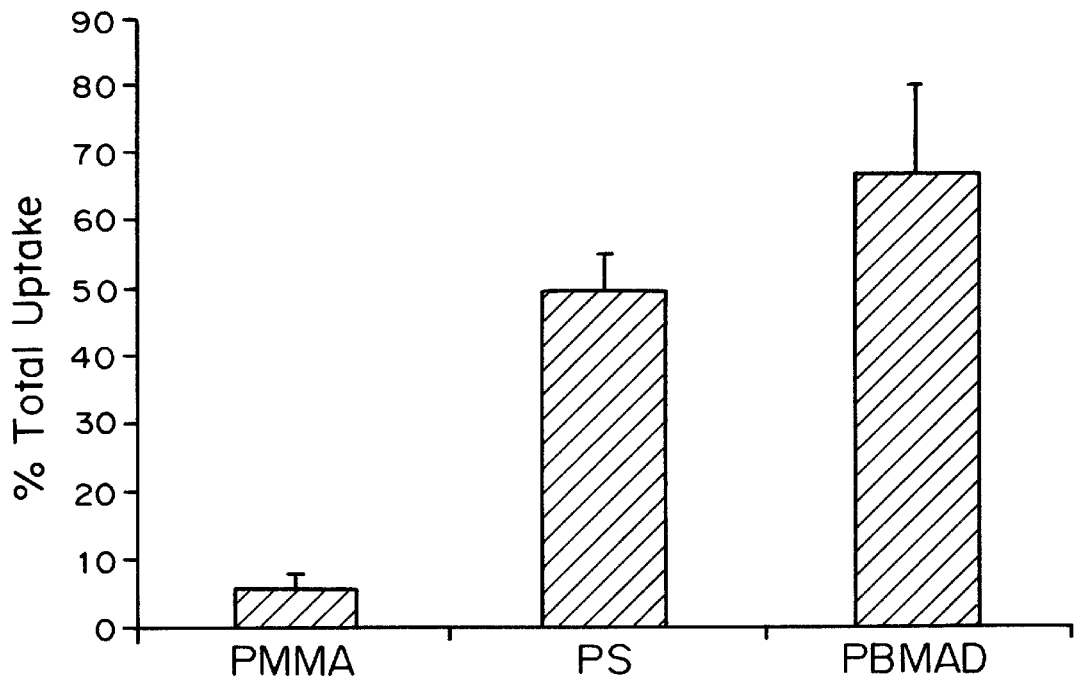
FIG. 8 is a bar graph plotting the % total intestinal uptake of PS, PMMA, and PMMA-BMAD nanospheres as determined using the protocol described in Example 4. Delivering 500 nm PS, PMMA and PMMA-BMAD nanospheres locally to the rat jejunum for a 5-hour period resulted in uptake of 45.8±8.6%, 5.8±1.9% and 66.9±12.9% the administered dose, respectively.

Delivering 500 nm PS, PMMA and PMMA-BMAD nanospheres locally to the rat jejunum for a 5-hour period resulted in a total intestinal uptake of 45.8±8.6%, 5.8±1.9% and 66.9±12.9% the administered dose, respectively, as shown in FIG. 8.

Analysis of the bioadhesion and intestinal uptake data reveals that the highly bioadhesive formulation (PMMA-BMAD nanospheres) resulted in a significantly greater intestinal uptake than the non-bioadhesive formulation (PMMA nanospheres). The most bioadhesive PMMA-BMAD double-walled nanoparticles resulted in a 66.9±12.9% intestinal uptake. This represented a more than six-fold increase in total intestinal uptake over the non-bioadhesive model (PMMA).

Comparison of bioadhesion and total intestinal uptake results revealed a direct correlation with a 2.5-fold increase in bioadhesion resulting in a >10-fold increase in total intestinal uptake. Comparison of the bioadhesion measurements to the total intestinal uptake showed a strong linear correlation regardless of whether the nanosphere formulations were measured ($R^2$=0.9558) or the bioadhesion of the bulk materials were measured ($R^2$=0.9998).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of increasing the uptake of an agent at a site in the gastrointestinal tract of a patient in need of treatment, comprising orally administering to the patient a composition comprising particles, wherein the particles comprise nanoparticles and a coating,
    wherein the nanoparticles comprise one or more active agents encapsulated in a non-bioadhesive polymeric material, and
    wherein the coating comprises a bioadhesive polymeric material with one or more of the following properties:
        (a) a higher adhesion to freshly excised rat intestinal tissue, as measured in terms of fracture strength, than polymethyl methacrylate (PMMA);
        (b) a lower contact angle with rat mucin than PMMA; and
        (c) when formed into spherical particles, exhibits a higher binding ratio to the jejunum, as measured by the everted sac method, than PMMA nanoparticles of substantially equivalent mean particle size, and wherein the bioadhesive polymeric material does not contain a metal compound,
    wherein the nanoparticles are taken up into the site in the gastrointestinal tract, and
    wherein the total intestinal uptake of the nanoparticles is increased by more than 40%, as compared to the total intestinal uptake of the nanoparticles from the same composition in absence of the bioadhesive polymeric material.

2. The method of claim 1, wherein the intestinal uptake of the nanoparticles is increased by more than 50%, as compared to the total intestinal uptake of the nanoparticles from the same composition in absence of the bioadhesive polymeric material.

3. The method of claim 1, wherein the bioadhesive polymeric material has the following properties:
    (a) an adhesion to freshly excised rat intestinal tissue, as measured in terms of fracture strength, that is equivalent to or greater than polystyrene (PS); and
    (b) a contact angle with rat mucin that is equivalent to or lower than PS; and
    (c) when formed into spherical particles, exhibits a binding ratio to the jejunum, as measured by the everted sac method, that is equivalent to or greater than PS particles of substantially equivalent mean particle size.

4. The method of claim 2, wherein the bioadhesive polymeric material is selected from the group consisting of poly(butadiene maleic anhydride-co-L-dopamine), polymer blends comprising poly(butadiene maleic anhydride-co-L-dopamine), copolymers comprising poly(butadiene maleic anhydride-co-L-dopamine), poly(fumaric-co-sebacic)anhydride, polymer blends comprising poly(fumaric-co-sebacic) anhydride, copolymers comprising poly(fumaric-co-sebacic) anhydride, and combinations thereof.

5. The method of claim 1, wherein the agent is selected from the group consisting of diagnostic agents, antibodies, amino acids; analgesics; anti-anginal agents; antibacterials; anticoagulants; antifungals; antihyperlipidemics; anti-infectives; anti-inflammatory agents; antineoplastic agents, anti-ulcerative agents; antivirals; bone resorption inhibitors; cardiovascular agents; hormones; peptides; proteins; genes; nucleic acids; hypoglycemic agents; immunomodulators; immunosuppressants; and wound healing agents.

6. The method of claim 1, wherein the particles are multi-walled particles comprising a core layer encapsulating the one or more active agents and a shell layer,
    wherein the core layer is a non-bioadhesive polymer and the shell layer is or is coated with the bioadhesive polymer.

7. The method of claim 1, wherein the particles are suspended or dispersed in a pharmaceutically acceptable carrier comprising a bioadhesive polymer matrix.

8. The method of claim 7, wherein the bioadhesive polymer matrix comprises a polymeric material selected from the group consisting of polyhydroxy acids, polystyrene, polyhyaluronic acids, casein, gelatin, gluten, polyanhydrides, polyacrylic acid, alginate, chitosan; polyacrylates; polyacrylamides; poly(fumaric-co-sebacic)acid, poly(biscarboxyphenoxy propane-co-sebacic anhydride), polyorthoesters, and blends and copolymers thereof.

9. The method of claim 6, wherein the particles are formed by a method comprising the steps of:
    (a) dissolving a core polymer in an effective amount of a core polymer solvent;
    (b) dissolving a second polymer in an effective amount of a second polymer solvent; wherein the second polymer solvent is solvent for the second polymer and is a non-solvent for the core polymer and wherein the core polymer solvent is a solvent for both the core polymer and the second polymer;
    (c) combining the solutions of (a) and (b) to form a polymer mixture; and
    (d) adding to the polymer mixture a non-solvent for the core polymer and second polymer to form multi-walled particles.

10. The method of claim 9, further comprising dissolving or dispersing the agent in the effective amount of the core polymer solvent in step (a), wherein the core polymer, agent, and core polymer solvent form a mixture having a continuous phase, and wherein the core polymer solvent is the continuous phase.

11. The method of claim 9, wherein the second polymer is the bioadhesive polymer, and wherein the multi-walled a particles are double-walled particles.

12. The method of claim 9, further comprising after step (c) and prior to step (d), adding to the polymer mixture a shell polymer solution, comprising a shell polymer dissolved in an effective amount of a shell polymer solvent, wherein the shell polymer solvent is a solvent for the shell polymer and is a non-solvent for the core polymer and the second polymer.

13. The method of claim 12, wherein step (d) forms triple-walled particles.

14. The method of claim 9, wherein the volume ratio of the solvent mixture to the non-solvent is between 1:5 and 1:1,000,000.

15. The method of claim 9, wherein the concentration of the core polymer in the core polymer solution is less than 20% weight per volume, and wherein the concentration of the second polymer in the second polymer solution is less than 20% weight per volume.

16. The method of claim 9, wherein the core polymer is a biodegradable polymer.

17. The method of claim 16, wherein the core polymer is a polyester selected from the group consisting of polylactide, polyglycolide, and poly(lactide-co-glycolide) (PLGA), and combinations thereof.

18. The method of claim 6, wherein the particles comprise a core polymer and a shell polymer, wherein the shell polymer is a bioadhesive polymer selected from the group consisting of poly(butadiene-maleic anhydride-co-L-DOPA), poly(ethylene-maleic anhydride-co-L-DOPA) and combinations thereof.

* * * * *